United States Patent [19]

Brown

[11] Patent Number: 5,678,571
[45] Date of Patent: Oct. 21, 1997

[54] METHOD FOR TREATING MEDICAL CONDITIONS USING A MICROPROCESSOR-BASED VIDEO GAME

[75] Inventor: Stephen J. Brown, Mountain View, Calif.

[73] Assignee: Raya Systems, Inc., Mountain View, Calif.

[21] Appl. No.: 247,716

[22] Filed: May 23, 1994

[51] Int. Cl.[6] .................................................. A61B 19/00
[52] U.S. Cl. ........................................ 128/898; 128/905
[58] Field of Search ............................ 128/897-98, 668, 128/905; 364/413.02–413.11

[56] References Cited

U.S. PATENT DOCUMENTS 5,307,263  4/1994  Brown .................................. 364/413.02

*Primary Examiner*—John P. Lacyk
*Attorney, Agent, or Firm*—Lumen Intellectual Property Services

[57] ABSTRACT

Method for treating a medical condition in a human patient comprising choosing a psychological strategy for treating the medical condition, encoding electronic instructions for an interactive video game in such a way that the interactive video game implements the psychological strategy, loading the electronic instructions into a microprocessor-based unit (10, 30) equipped with a display (14, 34) for displaying the interactive video game and with an patient input device (16, 36a, 36b, 36c, 36d, 36e) for receiving responses to the interactive video game from the human patient, and instructing the human patient how and when to use the microprocessor-based unit (10) to play the interactive video game. The interactive video game contains instructions for a scoring procedure for quantitatively analyzing the medical condition of the human patient, and/or counseling instructions or self-care instructions. The video game can be used in conjunction with a physical parameter measuring device (54) connected to the microprocessor-based unit (10).

18 Claims, 12 Drawing Sheets

METHOD FOR TREATING MEDICAL CONDITIONS USING A MICROPROCESSOR-BASED VIDEO GAME

BACKGROUND

1. Field of the Invention

The present invention relates to the field of medical treatment, and in particular to the treatment of medical conditions in human patients with the aid of a microprocessor-based video game.

2. Description of Prior Art

Medical conditions associated with a patient's behavior pattern or well-being are typically evaluated and treated in therapy sessions conducted by a physician or a health care specialist. Depending on the ailment, a preliminary picture of the patient's condition may be available to the specialist in the form of answers to questionnaires or results of a battery of tests. This applies to psychological conditions such as schizophrenia, depression, hyperactivity, phobias, panic attacks, anxiety, overeating, and other psychological disorders. In fact, the number of diagnostic tests presently available for classifying these conditions is vast. Such tests rely on the patient to perform a self-examination and to respond candidly to a series of personal questions. Since most tests differ in their basic scientific assumptions the results obtained are not standardized and can not often be used to make meaningful case comparisons.

Consequently, the above-mentioned psychological conditions are fully diagnosed and treated in therapy sessions. In these settings the specialist can better evaluate the state of his patient and design appropriate, individualized treatment. Unfortunately, because of the amount of time required to do this, diagnosis and treatment are very expensive.

The actual therapeutic changes in the patient occur outside of therapy as the patient applies cognitive and behavioral strategies learned in therapy to problem encountered in day-to-day situations. Progress is predicated to a large extent on patient cooperation, discipline, and self-management. Diaries are employed to ensure patient compliance. Still, in many instances, lack of compliance to long-term therapy regimes presents a major obstacle to successful treatment. Children are a particularly difficult group of patients in this respect. Frequently, they lack the understanding, maturity, and perseverance required to successfully pursue a treatment plan.

In fact, it has recently been confirmed that in the case of anxiety the best treatment involves teaching the patients new ways of responding to old stimuli. Drugs may be used to blunt the physical aspects, but there is no data to confirm the positive effects of their long-term use. Meanwhile, treatment of depressions requires attentive counseling and listening to the patient. The same applies to treatment of personality disorders, obsessive-compulsive disorders, hysteria, and paranoia. Unfortunately, cost of treatment and compliance with suggestions made by the therapist are major problems, as pointed out above.

In difficult cases observation and comparison with criteria compiled in the Diagnostic and Statistical Manual of Mental Disorders—the standard classification text of the American Psychiatric Association—are the only recognized treatment alternatives.

There is also a wide variety of medical conditions, other than the above-mentioned psychological disorders, requiring extensive self-help and self-treatment by the patient. These conditions include addictions, compulsive behaviors, and substance abuse. Most common examples are smoking, gambling, and alcoholism. At the present time treatment for these medical conditions involves counseling, distraction techniques, and chemical replacement therapy. Ultimately, however, all of these methods depend on the cooperation of the patient and a large dose of self-motivation. This is especially important when the patient is in his or her own surroundings where the objects of their addition or compulsion are easily accessible.

Unfortunately, compliance with medical advice is notoriously poor, and gentle persistence may be necessary. Some physicians recommend that the entire family or other group of significant personal contracts in the patient's life should be involved with the patient's consent. This, of course, presents major problems and is a costly treatment method.

Some attempts have been made at using computers to diagnose and educate patients about their medical condition. Typically, these attempts have produced questionnaires which can be filled out on a computer, or educational programs telling the patient more about his or her medical condition. Unfortunately, these projects stop short of being sufficiently adapted to patient needs to help with treatment or therapy. In fact, health care professionals maintain that computers can never replace the sense of caring, of relatedness, which is the vehicle in which most therapy takes place.

OBJECTS AND ADVANTAGES OF THE INVENTION

In view of the above, it is an object of the present invention to provide a method for treating a medical condition by using a microprocessor-based video game to produce a better preliminary picture of the ailment, make therapy considerably less costly, and emphasize superior patient self-help responses.

Other objects of the invention are to enable treatment in the patient's own, private environment, provide a treatment method to which the patient can resort as the need arises, and ensure higher treatment compliance for all patients, and in particular children.

Finally, it is another object to provide a better method for standardization of treatment results for psychological disorders.

These and other objects and advantages will become more apparent after consideration of the ensuing description and the accompanying drawings.

SUMMARY OF THE INVENTION

Surprisingly, it has been found that in the case of psychological disorders, addictions, substance abuse, and compulsions one can successfully use treatment methods based on computer-generated video games. Such method for treating a medical condition in a human patient comprises the steps of: choosing a psychological strategy for treating the medical condition, encoding electronic instructions for an interactive video game in such a way that the interactive video game implements the psychological strategy, loading the electronic instructions into a microprocessor-based unit equipped with a display for displaying the interactive video game and with a patient input device for receiving responses to the interactive video game from the human patient, and instructing the human patient how and when to use the microprocessor-based unit to play the interactive video game.

The psychological strategy implemented by the interactive video game can involve a graphical game character faced with fictitious challenges representative of the patient's medical condition. The responses of the human patient to these challenges of the graphical game character can define the game success of the graphical game character. Moreover, the interactive video game can contain instructions for a scoring procedure for quantitatively analyzing the medical condition of the human patient. This enables a health specialist to draw comparisons between results obtained for different patients.

Besides psychological strategies the video game can also contain counseling instructions or self-care instructions. In fact, the video game can be used in conjunction with a standard monitoring device. To do this a monitoring device for measuring a physical parameter, e.g., blood glucose level for a patient with diabetes, is connected to the microprocessor-based unit. Then a second set of electronic instructions is encoded for operating said monitoring device, where the second set of electronic instructions is compatible with the first set of electronic instructions. Finally, the two sets of instructions are merged.

| LIST OF REFERENCE NUMBERS | |
|---|---|
| 10 | microprocessor-based unit |
| 12 | microprocessor |
| 14 | display screen |
| 15 | speaker |
| 16 | patient input device |
| 18 | memory |
| 20 | digital storage medium |
| 22 | interface |
| 24 | network link |
| 26 | network |
| 28 | network server |
| 30 | hand-held microprocessor unit |
| 32 | housing |
| 34 | display screen |
| 36a, b, . . . | input keys |
| 38 | program cartridge |

| -continued | |
|---|---|
| LIST OF REFERENCE NUMBERS | |
| 40 | connection cable |
| 42 | remote communication unit |
| 44 | communication line |
| 46 | clearing house |
| 48 | transmission line |
| 50 | facsimile machine |
| 52 | hospital computer |
| 54 | physical parameter measuring device |

Figure 1:
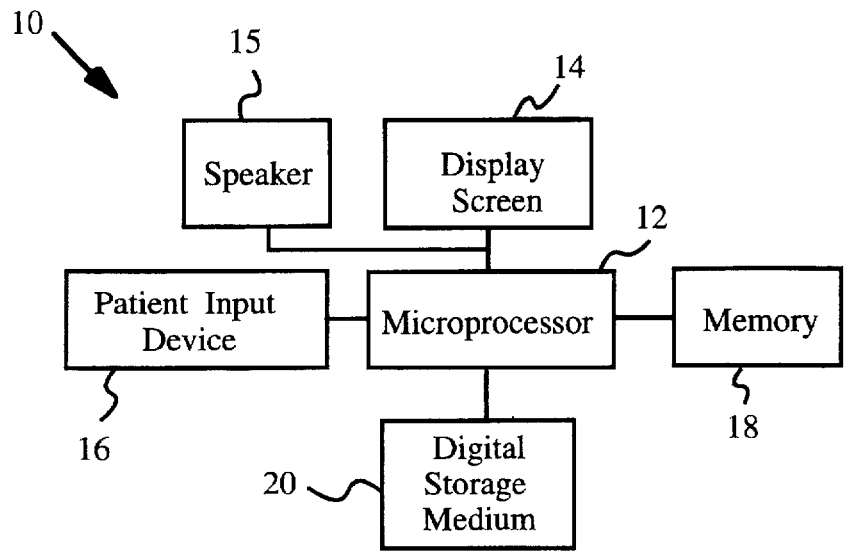
FIG. 1 is a block diagram of an autonomous computer system employed in the method according to the invention.
Figure 2:
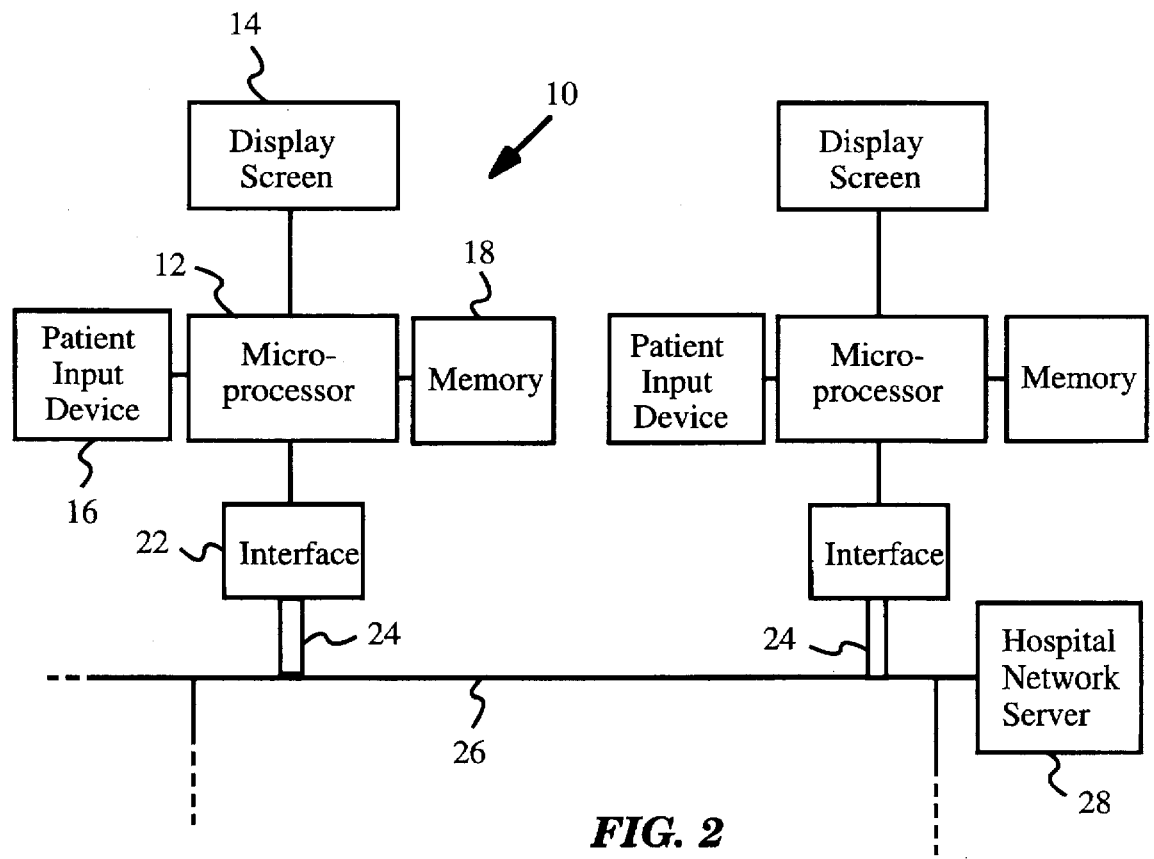
FIG. 2 is a block diagram of a computer network used in the method according to the invention.
Figure 3:
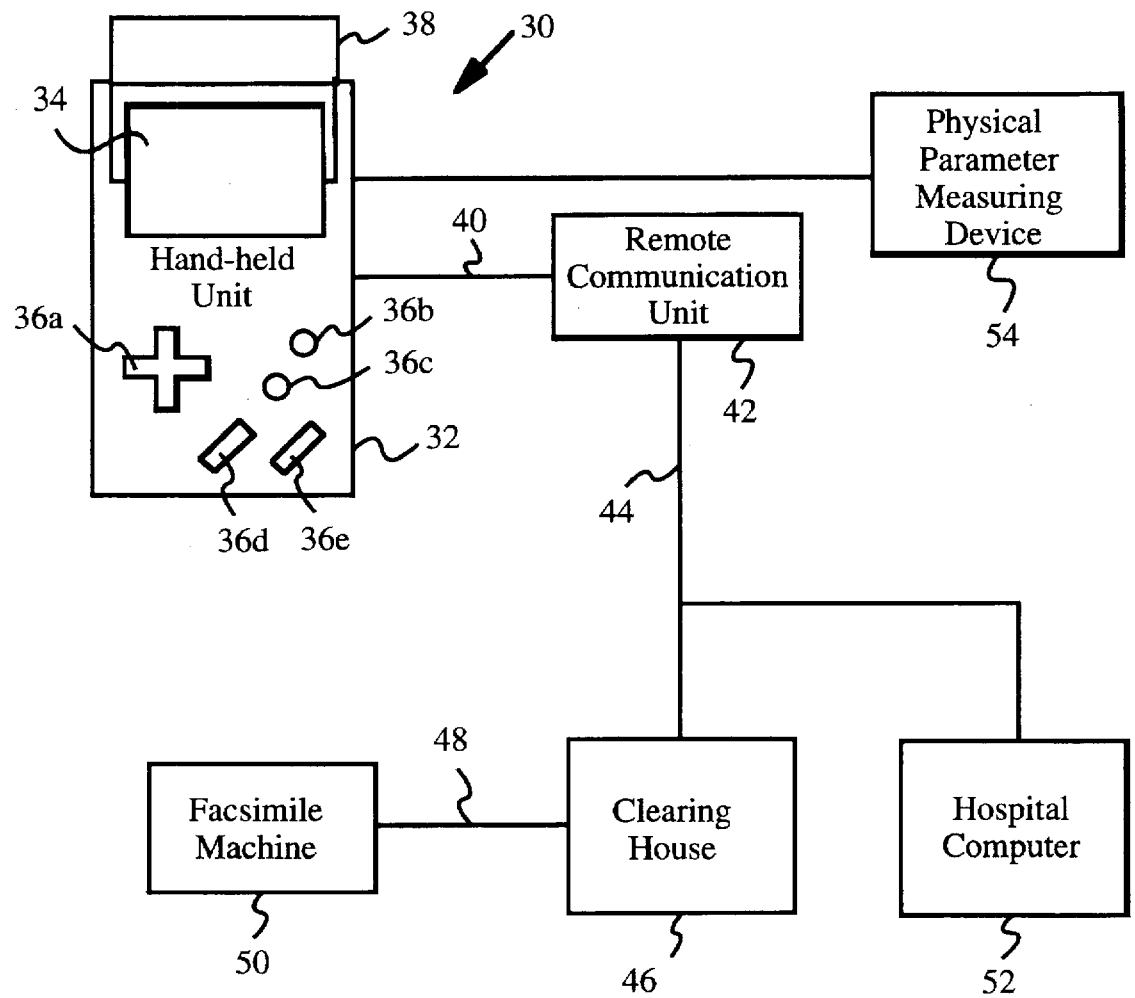
FIG. 3 is a block diagram of a system employing a hand-held: microprocessor unit for implementing the method of the invention.

DESCRIPTION OF PREFERRED EMBODIMENTS—FIGS. 1 to 3

FIG. 1 shows a block diagram representing a typical embodiment of a computer or microprocessor-based unit 10 capable of supporting video games for patient treatment. At the heart of unit 10 is a microprocessor 12. In addition to operations necessary to run unit 10, microprocessor 12 can process video data. Of course, in complicated systems the tasks of microprocessor 12 can be performed by a number of microprocessors. In the most preferred embodiment microprocessor 12 is a SUPER NINTENDO (TM) microprocessor.

A display unit or screen 14 is connected to microprocessor 12. The resolution and size of display screen 14 are sufficient to project visual images generated by video games. In a preferred embodiment screen 14 is a high-resolution video monitor or television screen. A speaker 15 for producing sounds associated with video games is hooked up to microprocessor 12 as well.

A patient input device 16 is also connected to microprocessor 12. Input device 16 can be a keyboard, joystick, mouse, button, trigger, light-pen, or the like, or combinations of these devices. A suitable choice of input device 16 is made based on the video game displayed on display screen 14 and the medical conditions of the human patient. The selected input device 16 will thus permit the patient to actively participate in the video game.

Additionally, microprocessor-based unit 10 has a memory 18, which is in communication with microprocessor 12. Memory 18 contains data required by microprocessor 12 to operate unit 10. While in the exemplary embodiment illustrated in FIG. 1 memory 18 consists of a single unit, configurations with many memory units of different types are possible.

Unit 10 is also connected to a digital storage medium 20 and appropriate data reading devices (not shown). Digital storage medium 20 can be a hard-disk, a floppy disk, a compact disk (CD), a cartridge, a network storage unit, or any other convenient medium capable of storing electronic instructions for running a video game on unit 10. In the preferred embodiment storage medium 20 is a high-storage-capacity CD disk. The ability to hold a large amount of data is a prerequisite for storing large video game programs.

FIG. 2 is a block diagram of a computer network for practicing the video game treatment method. Individual microprocessor-based units 10 on the computer network are substantially the same as in FIG. 1, therefore the same reference numbers are used for corresponding parts. Instead of digital storage medium 20, units 10 in FIG. 2 have a network interface 22 equipped with a network link 24. Link 24 connects microprocessor 12 to network 26 via interface 22. In a preferred embodiment network 26 is a separate hospital network adapted to patient use.

On the hospital side network 26 is connected to a hospital network server 28. Server 28 is capable of exchanging data, in particular video game data, with each unit 10 connected to network 26. Server 28 is also connected to computers used by monitoring personnel and physicians at the hospital (not shown).

The block diagram of FIG. 3 shows a particularly convenient embodiment for implementing the diagnosis and treatment method. A hand-held microprocessor unit 30 is equipped with a video display 34 and a number of input switches or keys 36a, 36b, 36c, 36d, and 36e, which are mounted on a housing 32. A set of components including a microprocessor, memory circuits, and circuitry that interfaces keys 36a, 36b, 36c, 36d, and 36e with the microprocessor is installed inside housing 30 but not shown in FIG. 3. Stored in the memory of programmable hand-held microprocessor unit 30 is a set of electronically encoded program instructions. These instructions establish a data protocol that allows hand-held microprocessor unit 30 to perform digital data signal processing and generate desired data or graphics for display on display unit 34 when a program cartridge 38 is inserted into a slot or other receptacle in housing 32. That is, cartridge 38 of FIG. 3 includes read-only memory data encoding the instructions for playing a particular video game.

In the most preferred embodiment hand-held microprocessor unit 30 is the compact game system manufactured by Nintendo of America, Inc. under the trademark "GAME BOY". This device is particularly simple. Furthermore, unit 30 is hooked up to a remote communication unit 42 via a connection cable 40. Preferably, for reasons of convenience, unit 42 can be a modem capable of communicating over telephone lines, or a radio-frequency transceiver capable of wireless sending and receiving of information. Of course, any other common telecommunications devices can also be used. It is assumed in the preferred embodiment shown in FIG. 3 that unit 42 is a high-speed modem.

A communication line 44, in this event a telephone line, connects unit 42 to a data clearing house 46 and hospital computer 52. This set-up establishes an efficient data pathway from hand-held microprocessor unit 30 to clearing house 46 and hospital computer 52. Clearing house 46 is capable of classifying data and sending appropriate messages concerning the patient's medical condition to a health care professional or physician. In the preferred embodiment clearing house 46 is connected by transmission line to a facsimile machine 50 standing in the office of a physician or health care professional.

A physical parameter measuring device 54, e.g., a glucose blood meter or a respiratory flow meter is also connected to hand-held unit 30. Device 54 is designed for patient self-monitoring while playing a video game. For this purpose device 54 is capable of downloading measurement data into hand-held unit 30. Appropriate choice of device 54 is made by the physician depending on the other hardware and intended video game for patient treatment.

OPERATION—FIGS. 1 to 10

Figure 4:
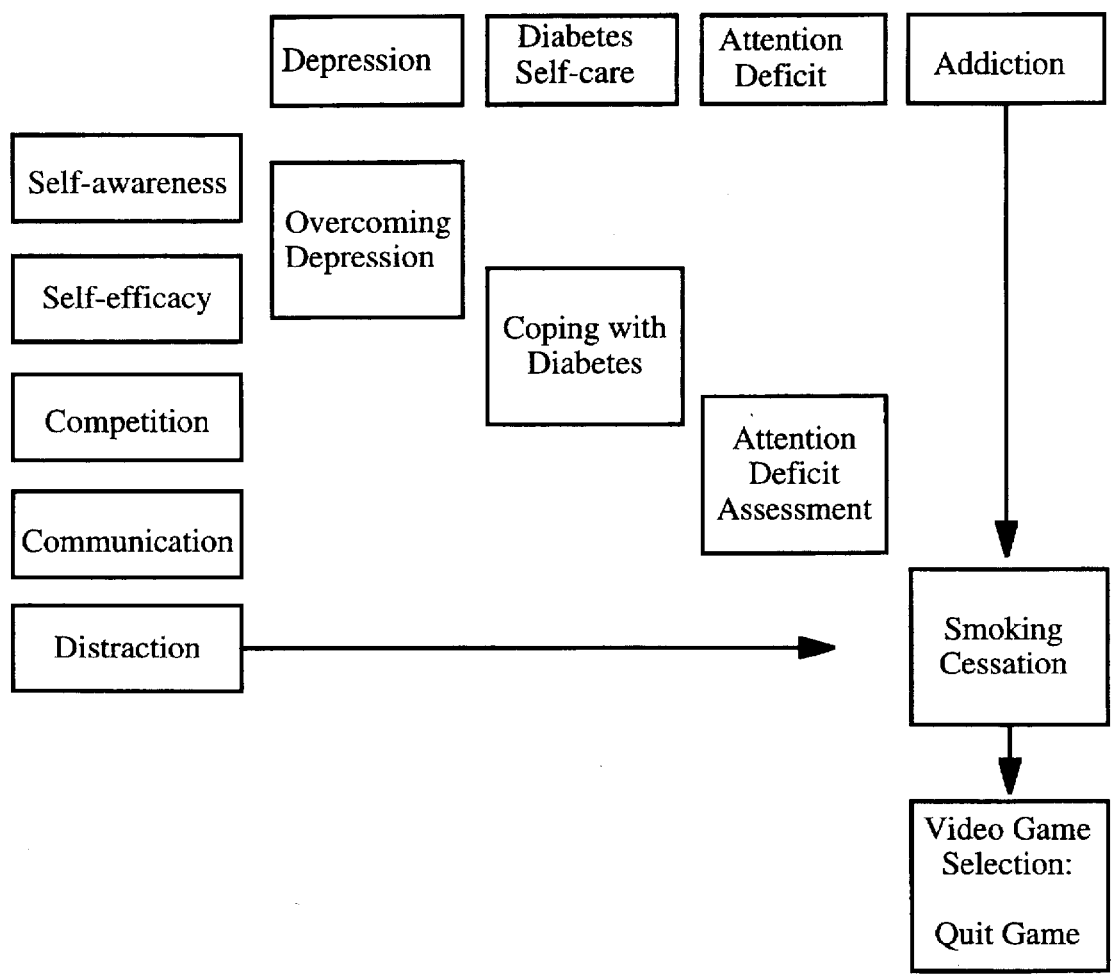
FIG. 4 is a flow chart illustrating how to select an appropriate video game treatment for some common medical conditions.

Before using microprocessor-based unit 10 shown in FIG. 1, a patient will first visit a physician or health care professional to evaluate his or her medical condition. The physician will diagnose the condition and choose the proper treatment based on patient needs. The flow chart in FIG. 4 shows the psychological strategies which the physician can select for treating depression, attention deficit, addiction, and diabetes. The psychological strategies listed include self-awareness training, self-efficacy training, competition, communication, and distraction. Of course, other well-known strategies such as positive reinforcement, negative reinforcement, role-playing, etc. can be employed as well. In addition to these, the psychological treatment strategy can include counseling methods and self-care instructions. Moreover, the treatment strategies can be combined as shown For example, as shown in FIG. 4, overcoming depression is best ensured by a therapy which joins self-awareness training with learning self-efficacy to regain control over one's life. In the particular case highlighted with two arrows the medical condition to be treated is an addiction, e.g., smoking or alcoholism, and the appropriate psychological strategy for treating this condition is distraction.

Once the psychological treatment strategy has been selected, the physician will choose an appropriate interactive video game program comprising this strategy. Examples of video games based on the most common psychological strategies will be given in the specific examples to follow. Meanwhile, the program itself consists of electronically encoded instructions in data storage medium 20 (FIG. 1). The video game program is loaded from this medium 20 into microprocessor 12 and memory 18 of unit 10. In the preferred embodiment this is accomplished most conveniently by a CD disk drive (not shown) since digital storage medium 20 is a CD disk. The patient receives unit 10 prepared in this way and is instructed by the physician how and when to play the video game. Of course, the physician may also load several video games at once and instruct the patient when to play each one. Depending on the type of video game and the patient's capabilities, the physician will also determine what patient input device 16 should be employed in playing the game.

The patient takes home unit 10 prepared in this manner, and follows the prescribed treatment by playing the video game. Once in operation, unit 10 displays the graphical video game on display screen 14 and receives input through patient input device 16. The beneficial effect of playing the game is thus available to the patient at any time in his own environment.

The process described above can also be accomplished with the computer network shown in FIG. 2. Here, appropriate treatment programs can be loaded directly into unit 10 used by the patient while he is at home. To do this the physician selects the appropriate video game, determines its destination address, i.e., unit 10, and places the game on hospital network server 28. The designated unit 10 then retrieves the video game via network 26 and loads it into microprocessor 12 and memory 18. This is done with the aid of network link 24 and interface 22.

A particularly convenient method for delivering a video game to the patient is shown in FIG. 3. Hand-held microprocessor unit 30 receives video games directly from hospital computer 52. The video game is transmitted through communication line 44 and received by remote communication unit 42. Unit 42 downloads the game directly into hand-held unit 30 via connection cable 40.

Hand-held unit 30 in FIG. 3 also communicates with clearing house 46 using communication line 44. Thus, the patient's progress in playing the video game can be directly monitored, e.g., by checking the video game scores. This information is screened, classified, and sorted by clearing house 46. Then an abstract or report is transmitted through transmission line 48 to facsimile machine 50 which can be conveniently located in the physician's office.

Unit 30 shown in FIG. 3 can also be used by the patient to check his medical condition. To do this the patient follows instructions embedded in the video game which tell him to connect to unit 30 his measuring device 54, e. g., blood glucose meter in the case of a patient with diabetes. Of course, unit 30 and device 54 may also be hooked up permanently by the physician. Then the video game instructions tell the patient that to continue playing he needs to perform a regular self-measurement using device 54.

For a patient with diabetes this involves checking his blood glucose level by drawing a small blood sample into device 54. The individual steps for doing this are not a part of the invention. The measurement data is then downloaded into hand-held unit 30 to be used as input for the interactive video game session. Exemplary video game using this technique to collect data is described in example 4 below. Meanwhile, the blood glucose data is also passed through cable 40 to remote communication unit 42. From there the data follows the same path as described above for the video game score, and can be examined by the physician in the hospital.

The specific examples below describe exemplary microprocessor-based, interactive video games used for treating various medical conditions in human patients.

SMOKING—EXAMPLE 1

Figure 11A:
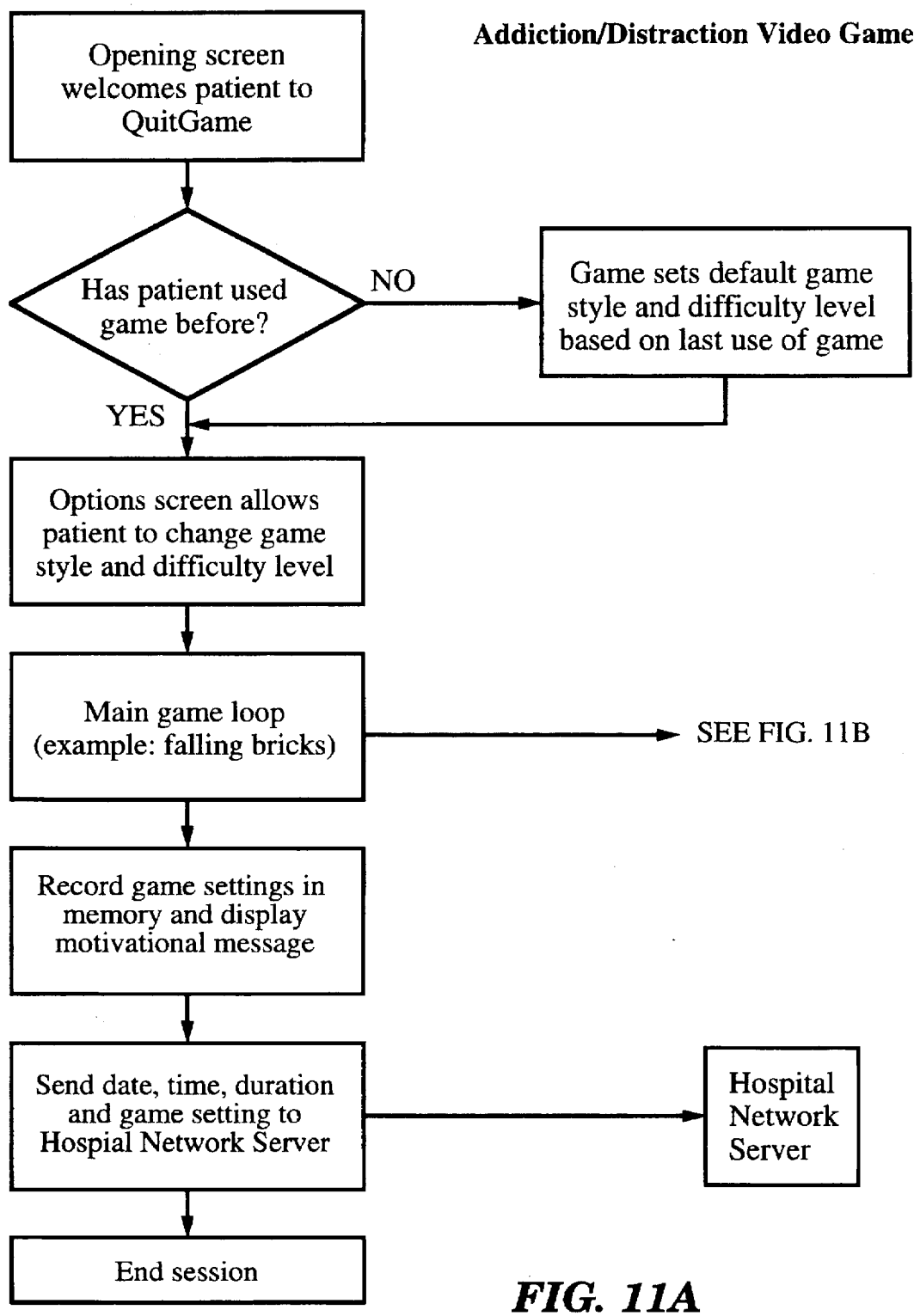
FIG. 11A is a general flowchart of an Addiction/Distraction Video Game.
Figure 11B:
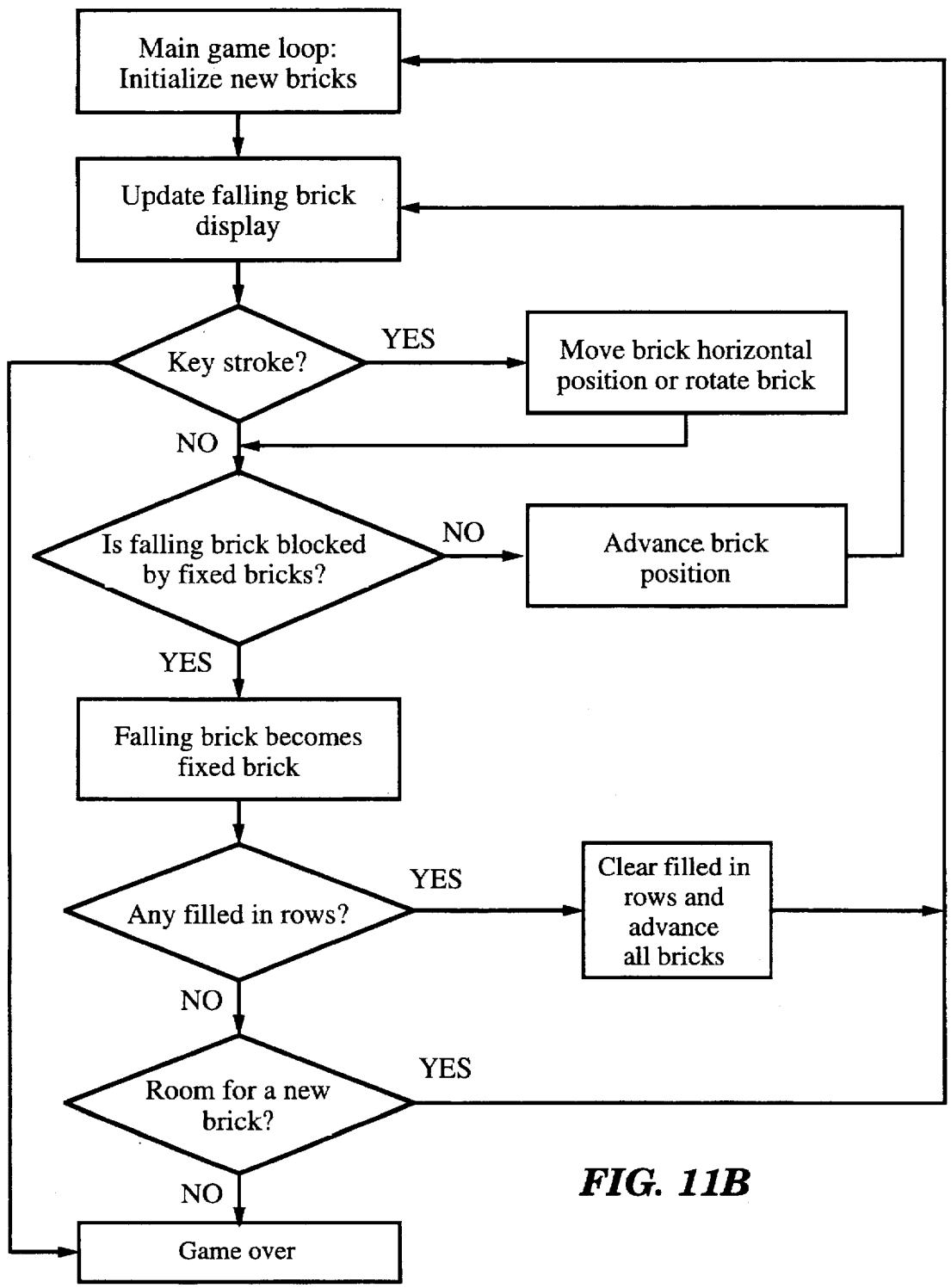
FIG. 11B is a detailed flowchart of the main game loop of the Addiction/Distraction Video Game of FIG. 11A.

The patient has a severe case of nicotine addiction. The physician determines, according to the flow chart in FIG. 4, that distraction is the best psychological strategy to induce the patient to quit smoking. Therefore, the physician prescribes playing the Quit Game, a video game containing a behavioral program based on distraction. This game contains graphical game characters engaging in various competitive activities upon proper input from the user. The smoker plays the game is played whenever he or she feels the urge to smoke. An exemplary game to provide such engaging distraction is shown in the flowchart illustrated in FIGS. 11A and 11B. In this particular embodiment the game distracts the player with falling bricks which have to be arranged in rows. During the game the main characters communicate to the patient instructions and simple strategies to quit smoking immediately and advise the user to take this approach, all within the context of the entertaining video game.

Alternatively, the game provides a timer and timeline for gradual reduction approaches to smoking cessation. Included among these programs are instructions for using nicotine patches. Built in notification will serve to remind smokers to shift to a lower dose patch. Once the smoker has quit, the video game will provide a coping/relapse prevention model by using distraction methods during periods of smoking urges.

A pilot study using the NINTENDO GAME BOY (R) as a tool to aid smoking cessation was highly successful. In the pilot project, seven smokers were give a Game Boy portable loaded with the Quit Game and instructed to use it any time they felt the urge to smoke. Six of the seven smokers successfully quit and were very enthusiastic about this approach.

An analogous video game strategy is followed in dealing with other substance abuse conditions, alcoholism, and obsessive compulsive disorders.

GROWTH DISORDER—EXAMPLE 2

Figure 12:
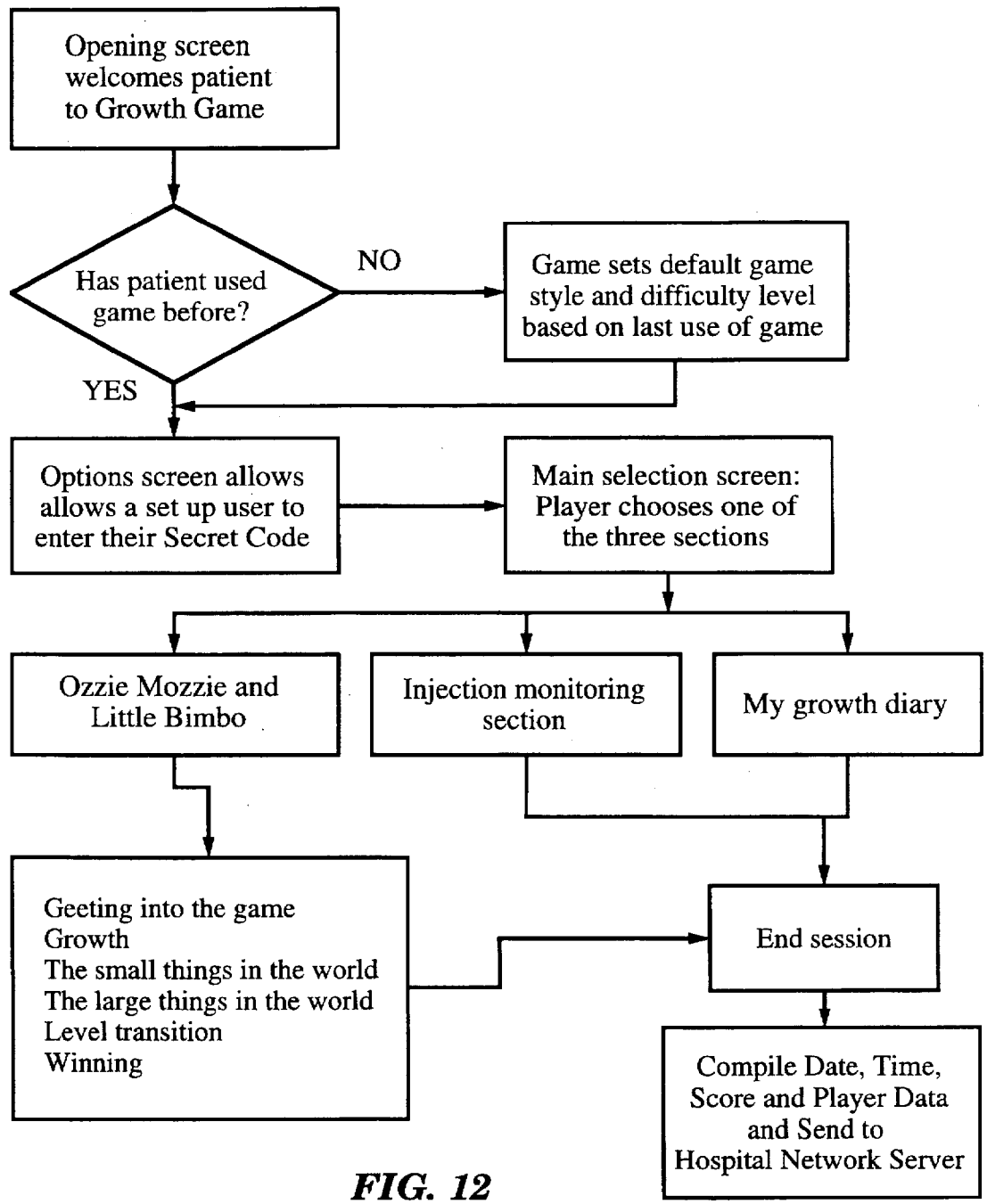

The physician diagnoses the patient with a growth disorder, such as Turner's Syndrome or a similar condition, requiring growth hormone treatment and a psychological treatment strategy for helping the patient cope with his or her condition. By following a selection process similar to the one indicated in FIG. 4, the physician prescribes a video game combining self-awareness training, self-efficacy, role-playing, counseling and competition. The flowchart of the Growth Game is provided in FIG. 12.

In the video game the graphical game character, Packy, is a young elephant who, like the patient, is on growth hormone therapy. The video game consists of three pans, each associated with a particular aspect of the treatment. In the first part Packy encounters obstacles which he must surmount, in the second he has to learn about growth hormone injections, and in the third one he has to keep a personal growth diary.

Figure 5:
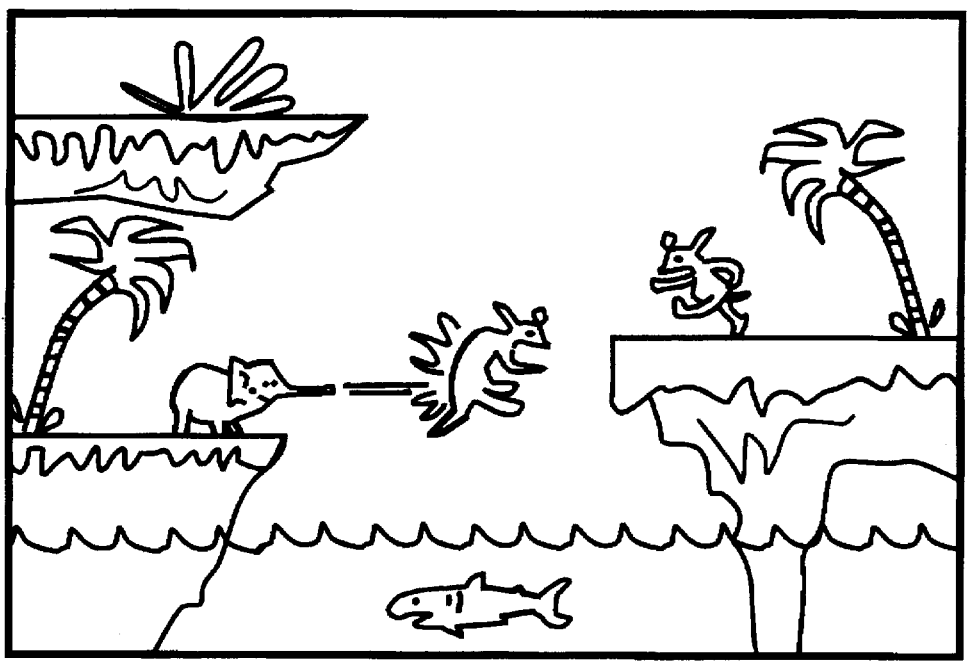
FIG. 5 is an exemplary screen of a video game for treating growth disorders according to the invention.

In the first part Packy learns about things that grow, from the smallest things in the world to the largest ones. In each level of this part Packy can pick up icons of OM (representing a growth hormone shot) for a boost of energy. When he gets this boost, he will grow to a larger size until the energy wears or he gets hit by one of his opponents. Every time Packy meets someone who challenges him he must push them away by pressing a button to lower his head and walking into them, or squirt them by pressing another button. The small antagonists push and squirt away easily, but the large ones require some strategy such as combining pushing and squirting. This stage is depicted in FIG. 5. In each level Packy will occasionally find obstacles that require a growth shot to get past. He will also occasionally encounter a guardian to the pathway that asks him questions from the information learned in the other two parts, i.e., the growth hormone injection instructions and the personal growth diary.

Figure 6:
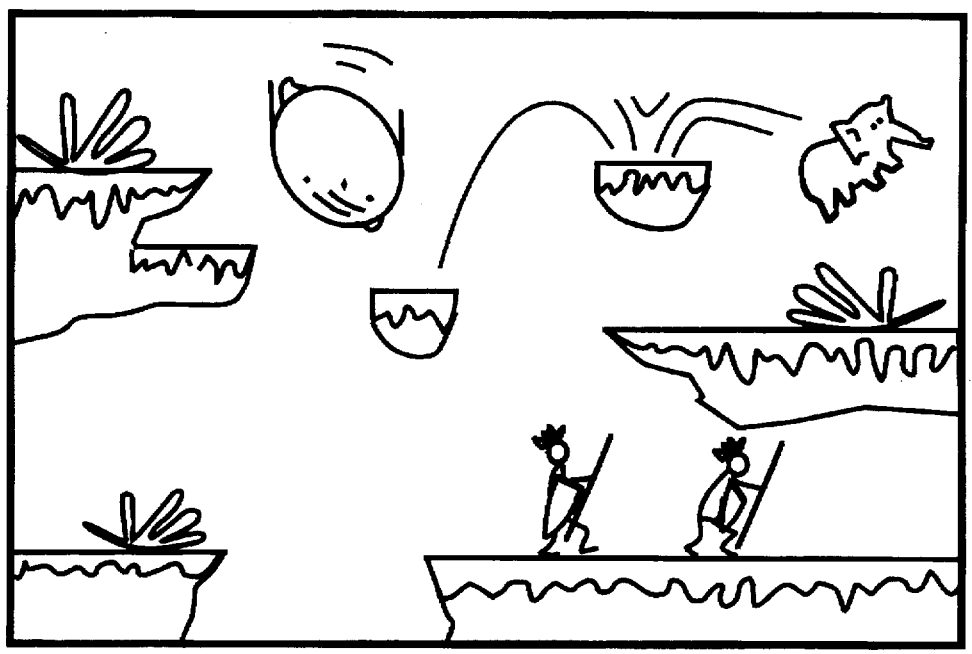
FIG. 6 is another screen of the video game of FIG. 5.

In another level of part one Packy has a dream in which he explores the world as a tiny creature. This scenario is illustrated in FIG. 6. He finds that he is very small himself, while all the surrounding items are very large. As he works his way to the end of this level he will encounter all types of animals and insects that are very small. This level will give Packy a feeling for what it is like to be really small. In the transition to the next level, Packy will wake up and see that he is still the same size, and grateful that he is not so small.

In the final level, Packy finds himself very large. He will be with the giant animals of the world. As he works his way through this level he will encounter all types of animals that are very large and the various types of obstacles they face in daily life. When Packy is bigger than the biggest elephant and cannot enter his home, he begins to realize the problems of being big.

Throughout his quest to feel comfortable with his growth, Packy is accompanied by his mosquito sidekick Zippy. His companion plays the role of a mentor and counsellor throughout the various levels of Packy's adventures.

In part two the patient will learn about preparing and administering doses of growth hormone. First, the user will see how to mix a dose, then prepare a pen for injecting the hormone, and then actually see how an injection is performed. In the game aspect of this part the user will be challenged to mix and administer a dose seven times (Monday through Sunday) and provide accuracy results.

The third part of the game is a growth diary where the patient records and sees various graphics displaying his or her personal progress.

Playing this game is reassuring and helps children overcome growth disorders by emphasizing self-awareness and self-efficacy training, role-playing, competition, and strategies embedded in the video game. Analogous video game strategy is also used to treat anxiety and hyperactivity disorders, various types of phobias, as well as enuresis.

DIABETES—EXAMPLE 3

Figure 7:
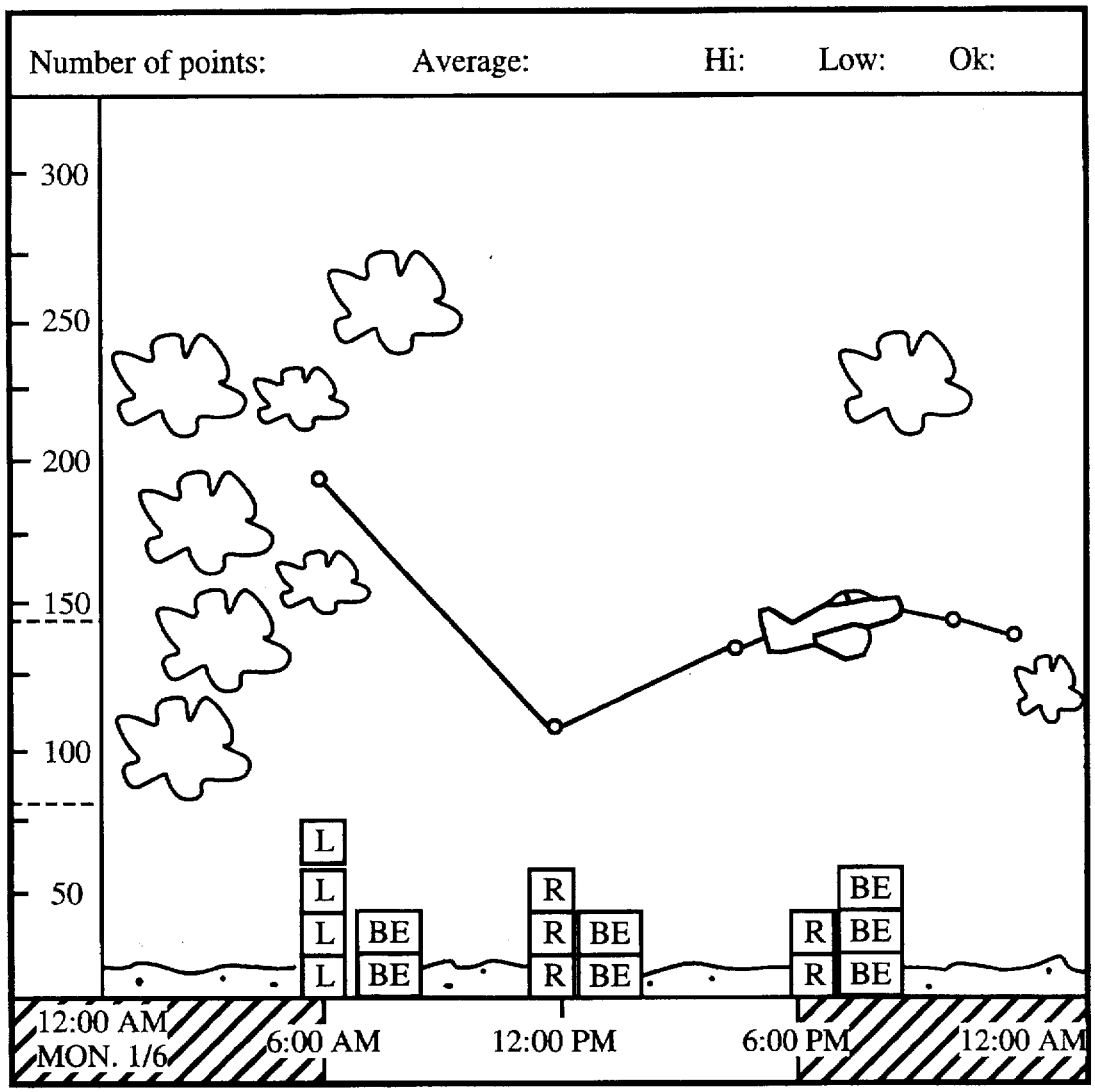
FIG. 7 is an exemplary screen of a video game for diabetes self-treatment according to the invention.
Figure 8:
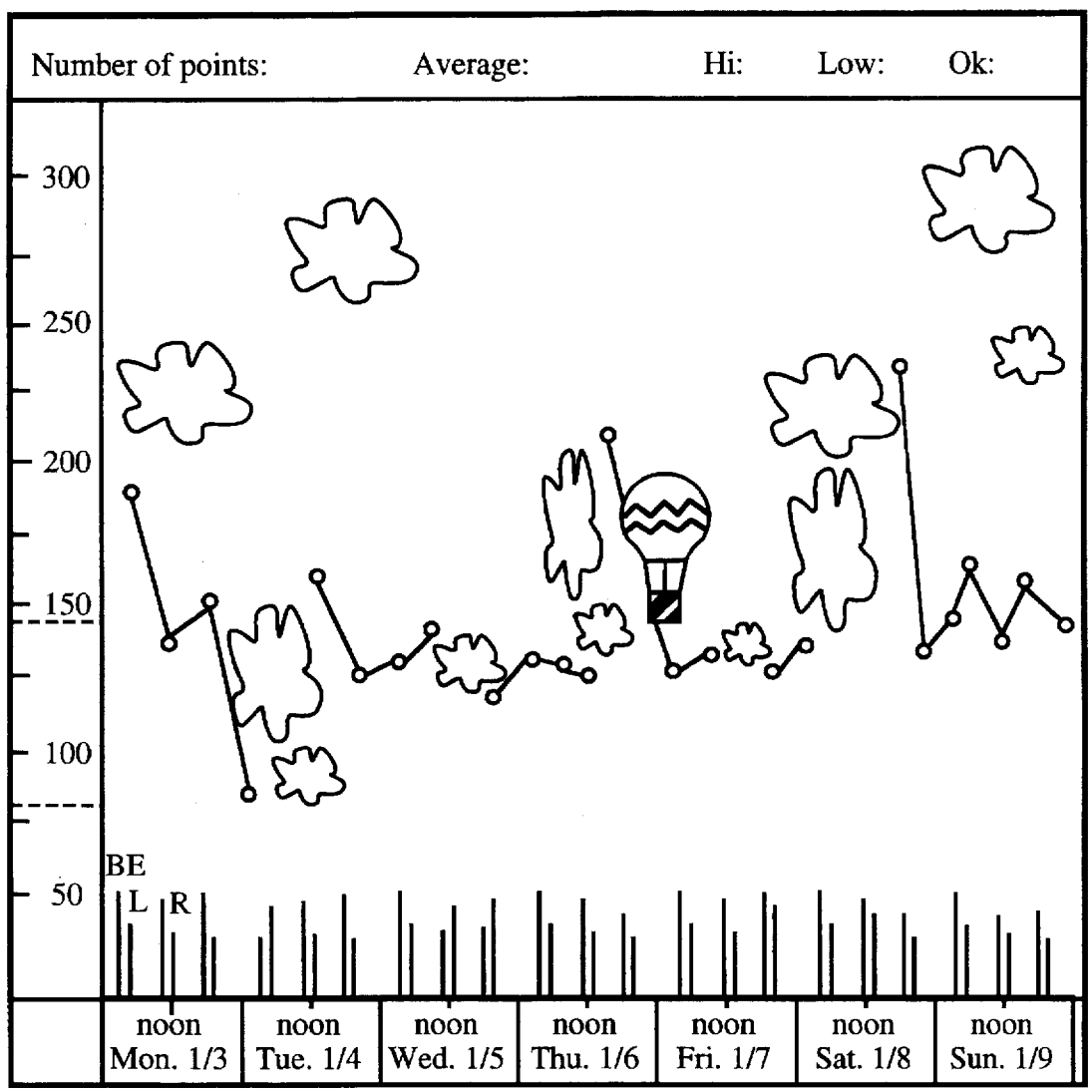
FIG. 8 is another exemplary screen for the video game FIG. 7.
Figure 13:
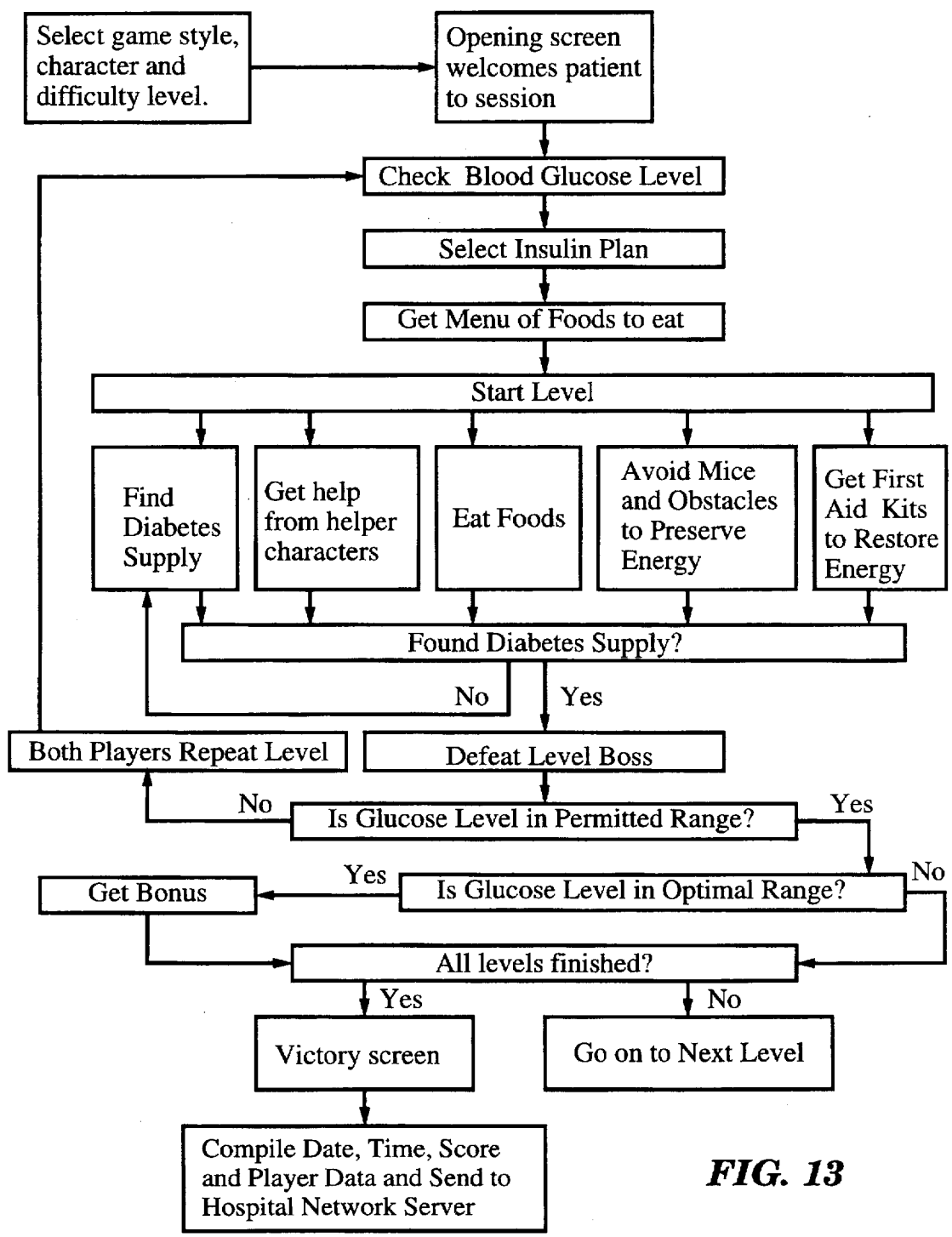

The patient is diagnosed with insulin-dependent diabetes. As treatment the physician prescribes insulin shots and a video game based on positive-reinforcement and self-management. In the video game the graphical game character is a pilot who has diabetes, just like the patient. The pilot needs to follow proper diet and exercise regimen to avoid crashing a plane or balloon which he is flying. The screens for the video game are shown in FIG. 7 and FIG. 8. The flowchart for this game is shown in FIG. 13. Eating wrong foods causes blood glucose level to increase and the plane or balloon starts gaining altitude uncontrollably. Eventually, above a certain threshold, the balloon or the plane spins out of control.

Figure 9:
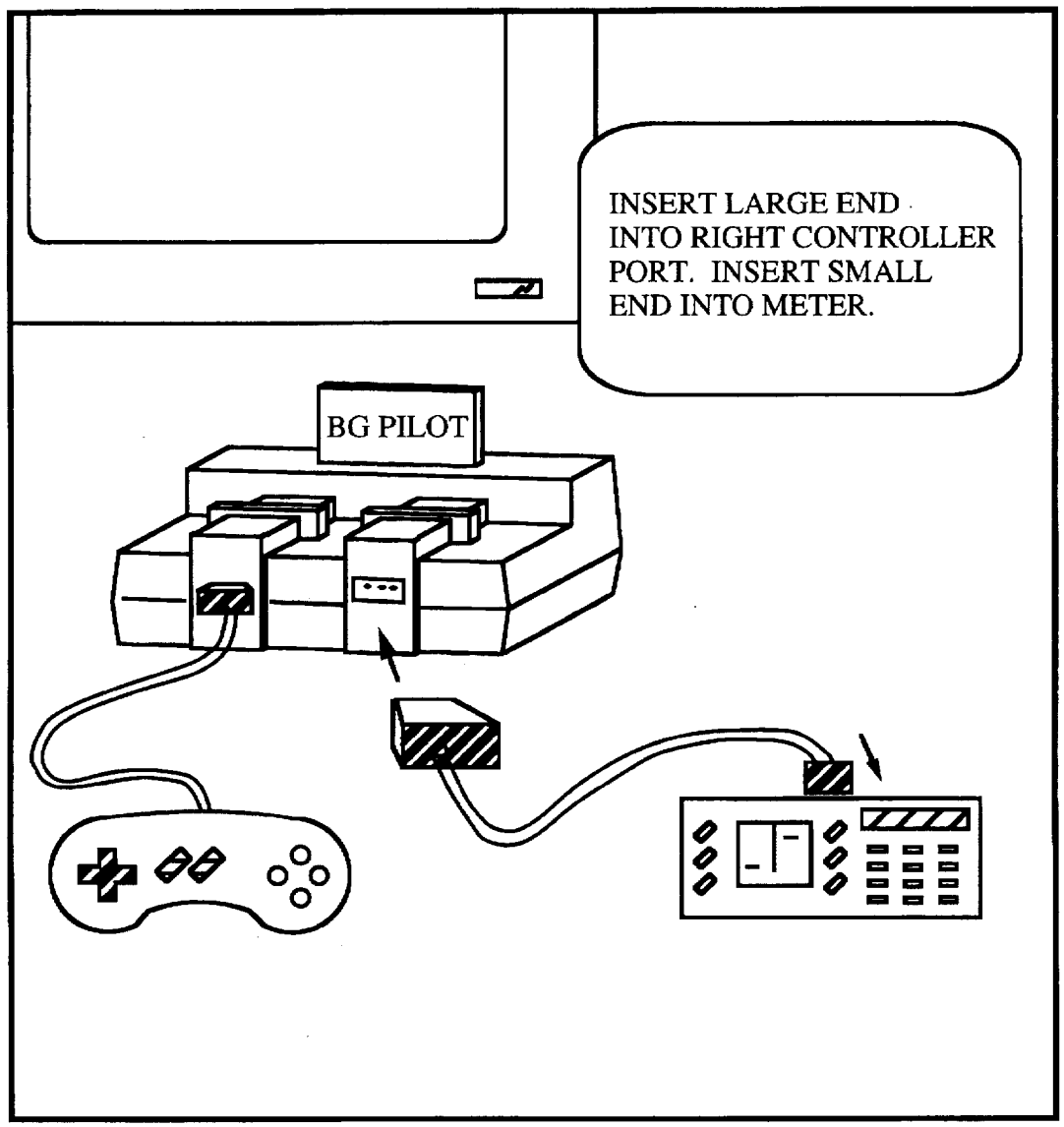
FIG. 9 is still another exemplary screen for the video game of FIG. 7.
Figure 10:
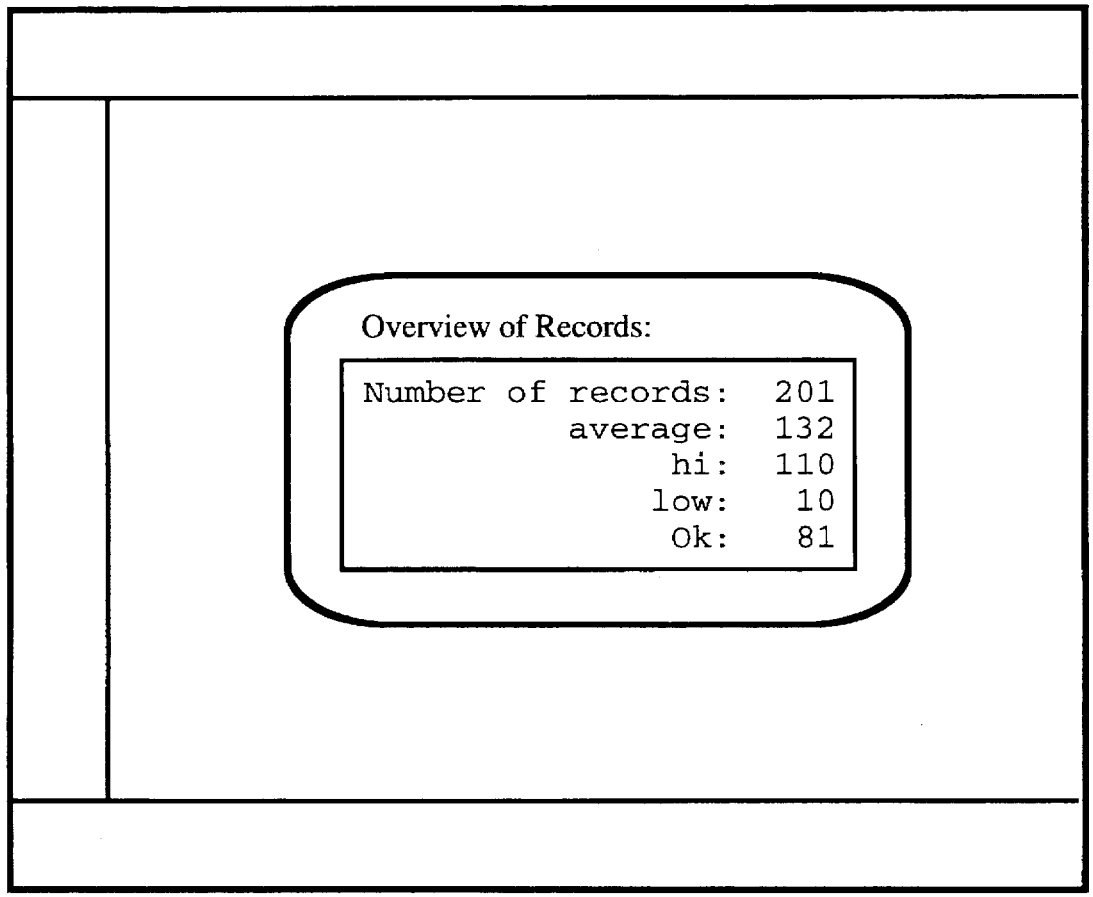
FIG. 10 is a screen indicating the blood glucose measurement results compiled for the video game of FIG. 7.

During the game the patient is requested to enter his own blood glucose level by using blood glucose meter 54. An exemplary set-up for doing this is shown in FIG. 9. The reading is used in the game and can also be transmitted to the hospital, as described in example 3. Also, the user can view his blood glucose readings in the form transmitted to the hospital and used in the game. An example of such reading for a number of measurement records is illustrated in FIG. 10.

If the user does not comply with the request for measuring and entering his blood glucose level the plane or balloon disappears behind clouds, representing uncertainty in blood glucose level. This is visualized by the clouds in FIGS. 7 and 8. The clouds obscure the pilot's vision and lead to collisions with objects in the plane's or balloon's path. Alternatively, if the blood glucose level drops below a minimum threshold, the plane or balloon crashes against the ground.

This positive reinforcement-based strategy, in which the blood glucose level is correlated to a game parameter, e.g., plane altitude, teaches the patient how to cope with his condition on a day-to-day basis while making blood glucose monitoring fun. It also produces higher treatment compliance rates, especially in children who need to learn early on about proper diabetes self-management.

NON-INSULIN DEPENDENT DIABETES MANAGEMENT—EXAMPLE 4

A video game treatment can be used for management of non-insulin dependent cases of diabetes (NIDDM). In such cases the video game is an interactive information resource, as well as a role-playing game. The game helps the patient, especially an adult patient, explore the topic of Staged Diabetes Management. The information is presented in hypertext format, allowing the patient to select a stage, read a brief overview of it, and select details to examine it in greater depth in desired. The game encourages active involvement in learning and provides opportunities to rehearse various health behaviors and see the consequences that result by observing what happens to a graphical game character who displays these behaviors.

The content of the game is based on the Staged Diabetes Management program, developed by the International Diabetes Center and Becton Dickinson & Company. The progressive set of stages ranges from least to most severe. For example, a patient in Stage I will learn to manage NIDDM through diet alone.

In the video game the user can configure the graphical game character in many ways. A checklist of chokes allows the patient to combine a variety of physical features and clothes, as well as specifics about the character's health status including weight, age, and medications taken.

The game character, and thus the patient, will make decisions in realistic settings such as restaurants and parties where rich foods are available. Also, an exercise plan will fit in with the character's busy schedule of family, community, and work commitments. This format provides the patient with a playful atmosphere in which choices which the patient faces in his or her own life can be rehearsed.

If blood glucose levels do not remain in the normal range in Stage I, then the patient is instructed by the graphical game character to advance to the next treatment steps, eventually arriving at the stage where the patient will be instructed to inject insulin to control blood glucose levels. The goal of the NIDDM game is to remain at Stage I.

Similar video games can help to deal with hemophilia, and other medical condition requiring the patient to be aware of his or her surroundings.

ASTHMA—EXAMPLE 5

A youngster diagnosed with asthma is given an asthma self-management game for hand-held unit 30. The graphical game character, a young dinosaur from the pre-historic town of Saurian, must cope with and manage his asthma. The game San character confronts common asthma triggers, while learning to recognize early warning signs of an oncoming asthmatic episode. Asthma management techniques including avoidance, relaxation, and medicinal inhalers are part of the daily routine for the young dinosaur who must return to his cave. The dinosaur runs, jumps, and shoots a squirt gun at oncoming triggers while conquering each level and mastering his condition. In addition to these inputs, the dinosaur requests the player to input the player's asthma condition by using physical parameter measuring device 54, which in this case is a respiratory flow meter. These data can then be transmitted to the physician as described above.

Playing the video game involving these real asthma triggers, relaxation techniques, etc., affects the mental state of the player to improve his own asthma management outside of video game sessions. This treatment based on role-playing and positive reinforcement makes the patient aware of the importance of prescribed drugs and teaches appropriate measures for dealing with the patient's condition in real life situations. (see Appendix A for Program).

EATING DISORDER—EXAMPLE 6

The physician determines that the patient suffers from an eating disorder causing the patient to gorge. The physician loads into the patient's microprocessor-based unit 10 or hand-held unit 30 a video game in which the graphical game character has to stay thin to survive. The game challenges confronting the game character include avoiding fatty foods to stay trim and eating a sufficient amount to combat dragons and surmount obstacles on his way. Doing this involves making choices about what food presented on the screen to eat, keep for later, or reject. Wrong food choices have immediate consequences in the graphical character's ability to survive. The game is scored according to the length of time the patient is capable of keeping his game character alive and obstacles the character overcomes.

The physician instructs the patient to play the game every time the patient feels an eating urge outside regular meal times. During a regular follow-up visit the doctor evaluates the patient's progress and checks the scores obtained in playing the video game. Based on the analysis of the sores the physician determines the severity of the problem and gets an insight into the patient's motivation to comply with the therapy. Sufficiently high scores reflect progress and readiness to proceed with the next treatment stage. At this point the physician may instruct the patient to play another video game designed for milder eating disorders or a game utilizing a different psychological approach, e.g., negative reinforcement or distraction.

DEPRESSION—EXAMPLE 7

A psychiatrist enrolls a patient in a series of home-based interactive video game sessions, which the patient accesses from his microprocessor-based unit 10 through hospital network 26. The video game is then transmitted from the hospital network server 28 to the patient's unit 10. The game involves interaction with a graphical game character resembling the Yoda character from the popular movie "Star Wars". Yoda acts as a counselor and mentor to the patient, preparing him for various trial episodes in the video game. Based on patient's scores in playing the video game sent, the physician reviews how the patient responds to video game counseling and prepares another game to be transmitted to the patient. This treatment method is part of an on-going therapy for mild to medium-severe depression. This approach is also used for schizophrenia and other purely psychological disorders.

SUMMARY, RAMIFICATIONS, AND SCOPE

The reader will thus see that I have presented a particularly simple method for treating medical conditions in human patients using a microprocessor-based video game. This method gives a better picture of the ailment through its standardized scoring procedure and makes the treatment much less costly by considerably reducing the number of therapy sessions with the physician or health care professional. In addition, video games emphasize superior treatment in the patient's own environment. This leads to self-help responses difficult to foster in therapy sessions. The patient recognizes the importance of medications and treatment regimens in an entertaining manner. Moreover, the patient participates actively in the treatment by following instructions embedded in the video game or even generating positive physiological responses due to stimuli presented in the video game.

The method of the invention also provides a treatment to which the patient can resort as the need arises. The intrinsic fun in playing video games ensures higher treatment compliance for all patients, and in particular children. The self-treatment instructions communicated by this method can be used to additionally induce patients to independently perform measurements of physical parameters associated with their medical condition.

Finally, the scoring of the video game provides an excellent standardized measure for evaluating treatment results and improving continued treatment. In carrying out the method the microprocessor-based system can be expanded to use any number of communications devices, monitoring set-ups, and other state-of-the-art medical equipment. Therefore, the scope of the invention should be determined, not be examples given, but by the appended claims and their legal equivalents.

APPENDIX A
ASTHMA VIDEO GAME SOURCE CODE

```
        LISTING

LONGA ON
        LONGI ON

;ÃÃÃÃÃÃÃÃÃÃÃÃÃÃÃÃÃÃÃÃÃÃÃÃÃÃÃÃÃÃÃÃÃÃÃÃÃÃÃÃÃÃÃÃÃÃÃÃÃÃÃÃÃÃÃÃÃÃÃ
; These are our local equates INITSCORE   =   $0000
INITBONUS   =   $5000
BUGTEST     =   7           ;Spank

CONTINUES   =   3

DEADTIME    =   30          ;time to delay at level end before fadeout
INITLIVES   =   3           ;lives
INITBBS     =   5           ;breath blasts
INITPFLOW   =   9           ;peakflow level

SPRITEPAL   =   SPRITE.PALSET

DUDEX=      120*PIXIZE      ;local screen coords
DUDEY=      120*PIXIZE

;IIIIIIIIIIIIIIIIIIIIIIIIIIIIIIIIIIIIIIIIIIIIIII
;
; GameLoop consists of main game control code, screen inits
;
;IIIIIIIIIIIIIIIIIIIIIIIIIIIIIIIIIIIIIIIIIIIIIII GameLoop    PROC dex
        dex             ;skip camp
        dex
        dex lda     LevelTbl,x      ;init screen IF      DEBUG
        bne     .0
        dec     DoneFlag        ;fake level!
        rts
.0      ENDIF phx ldy     #SCRN3Tbl       ; (all three of them)
        ldx     #^CITY1Tbl
        jsr     InitMode1 jsr     InitSprites     ;*** must do this
```

ASTHMA VIDEO GAME SOURCE CODE

```
        jsr     DrawStatus      ;update status info lda     Lives1
        bfl     .chkP2 lda     PlayerOne
        ldy     #PLAYERONE
        jsr     AddPlayer       ;add player sprite stx     PlayerID1
.chkP2
        ldx     #SA_SIZE-4
        stx     SpriteBeg       ;set start of monsters lda     PlayerTwo       ;one or two players?
        bfl     .oneP
        ldy     Lives2
        bfl     .oneP ldy     #PLAYERTWO
        jsr     AddPlayer       ; two- add appr. sprite stx     PlayerID2
.oneP
        ldx     #SA_SIZE-6
        stx     SpriteBeg       ;set start of monsters
        lda     VRAMBase
        sta     VRAMReset       ; & their VRAM base stz     ChkIdx jsr     SetLuminance
        ldx     #(CHKSIZE*3)-2  ;clear all three arrays
.clear
        stz     ChkType,x
        dex
        dex
        bpl     .clear lda     #1*PIXIZE
        sta     Gravity         ;current gravity strength jsr     NewDisplay      ;add monsters _NewCharSet #STATUSSET,#NORMALPAL    ;][ BUG FIX ][ plx
        lda     LevelTbl+2,x    ;get song for level
        _LoadSong

_APUCommand #DCOM_FADEIN,#$0101 jsr     FadeIn ; & show screen

;ÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄ
```

ASTHMA VIDEO GAME SOURCE CODE

```
InnerLoop
        lda     Top3Flag        ;update top of screen3?
        bfl     .vb
        jsr     UpdateTop       ; yes- do it
;ÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄ
.vb
        lda     VBFlag ;keep @ 30hz
        cmp     #2
        blt     .vb
        stz     VBFlag IF      0
;IIIIIIIIIIIIIIIIIIIIIIIIIIIIIIIIIIIIIIIIIIIIIIIIIIIIIII
; Check to see if a particular monster is in list ldx     #CHKSIZE-2
        stz     BTest
.loop
        lda     #BUGTEST
        cmp     ChkType,x       ;look for a matching type
        bne     .c1
        lda     #1*$400
        sta     BTest
.c1
        dex
        dex
        bpl     .loop   ;check entire array
        inc     OldWeapon1
;IIIIIIIIIIIIIIIIIIIIIIIIIIIIIIIIIIIIIIIIIIIIIIIIIIIIIII
        ENDIF
;ÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄ
; Update Sprs & check flags they set
        jsr     SetBG1 lda     PlayHit1
        beq     .no     ;keep player 1 safe after a hit
        dec     PlayHit1
.no
        lda     TrigHit1;don't trigger asthma too much
        beq     .no1
        dec     TrigHit1
.no1
        lda     PlayHit2
        beq     .no2    ;keep player 2 safe after a hit
        dec     PlayHit2
.no2
        lda     TrigHit2;don't trigger asthma too much
        beq     .no3
        dec     TrigHit2
.no3
        stz     HScrollSpd      ;clear speed
        stz     VScrollSpd jsr     RunActors       ;keep actors acting
```

Page # 3

ASTHMA VIDEO GAME SOURCE CODE

```
        lda     HScrollSpd
        beq     .h1         ;no adj. if not moving
        bmi     .hneg
        clc
        adc     HAdjust
        beq     .h2         ; insure good move
        bpl     .h1
        bra     .h2
.hneg
        sec
        sbc     HAdjust; (adjust for negative speeds)
        beq     .h2
        bmi     .h1
.h2
        lda     HScrollSpd      ;sanity check
.h1
        sta     Screen2+bHSpd       ;set screen 2 speed lda     VScrollSpd
        beq     .v1         ;no adj. if not moving
        bmi     .vneg
        clc
        adc     VAdjust
        beq     .v2         ; & insure correct move!
        bpl     .v1
        bra     .v2
.vneg
        sec
        sbc     VAdjust; (adjust for negative speeds)
        beq     .v2
        bmi     .v1
.v2
        lda     VScrollSpd      ;sanity check
.v1
        sta     Screen2+bVSpd       ;set screen 2 speed jsr     DoScroll        ;scroll main screen jsr     CheckBtns       ;check for control buttons lda     DoneFlag        ;until dead
        bfl     .chkDeath lda     DemoFlag        ;if demo is running, end at this point
        btr     endgame jsr     FadeOut lda     WhichBoss
        bfl     .showAsthma inc     WhichBoss
        bfl     .showInt inc     WhichBoss
        rts
```

Page # 4

ASTHMA VIDEO GAME SOURCE CODE

```
;         bra      endgame       ;this line was cause double flash on rex room end
.showAsthma
          lda      CurLevel
          cmp      #100
          beq      .rexo if       ARECORD
          jsr      ShowAsthmaRecord
          endif
          jsr      ShowBonus
.rexo
          bra      endgame
.showInt
          jsr      Intermission bra      endgame       ;don't reset peakflow
.chkDeath
          lda      DeathFlag     ; or done
          bpl      Scroll1
;         bfl      Scroll1 inc      DeadDelay
          lda      DeadDelay
          cmp      #DEADTIME
          btr      Scroll1
          stz      DeadDelay endgame HelpEnd
          _APUCommand #DCOM_FADE_AND_STOP,#$0101
.endout
          jmp      FadeOut       ; & then fade into the sunset ;ÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄ
; Scroll parallax background as required Scroll1
.now
          jsr      UpdateStatus  ;keep status info current lda      MonType       ;needed by AddMonster!
          bfl      .nom jsr      AddMonster    ;with info in buffers...
.nom
          jsr      SetBG2 lda      HConstSpd     ;always moving?
          bfl      .h3
.h5
          clc
          adc      HScrollSpd
.h4
          sta      HScrollSpd
.h3
```

ASTHMA VIDEO GAME SOURCE CODE

```
            lda     VConstSpd       ;always moving?
            bfl     .v3
.v4
            clc
            adc     VScrollSpd
            sta     VScrollSpd
.v3
            jsr     DoScroll        ;scroll the field stz     MoveV
            stz     MoveH jmp     InnerLoop ;IIIIIIIIIIIIIIIIIIIIIIIIIIIIIIIIIIIIIIIIIIIIIIII
; Routines for scrolling. These allow us to scroll the PARLX
; background according to our custom needs.
;
; ENTRY:    ScrollSpd set for V and H
;
; EXIT: none
;IIIIIIIIIIIIIIIIIIIIIIIIIIIIIIIIIIIIIIIIIIIIIIII DoScroll    PROC lda     VBFlag
            bfl     DoScroll lda     HScrollSpd
            bfl     .noscr2 jsr     ScrollHoriz     ;scroll horizontally
.noscr2
            lda     VScrollSpd
            bfl     .noud jsr     ScrollVert      ;scroll Vertically
.noud
            RTS

PROCEND

;IIIIIIIIIIIIIIIIIIIIIIIIIIIIIIIIIIIIIIIIIIIIIIII
; bring machine pieces together Intermission    PROC stz     MachStat
            jsr     ShowMachineScrn     ;subliminally show scenes of graphic sex lda     CurLevel
            sec
            sbc     #4
            lsr
            lsr
```

ASTHMA VIDEO GAME SOURCE CODE

```
        lsr
        lsr
        asl
        tax
        lda     MachPieceTbl,x
        ldx     #252*PIXIZE
        ldy     #192*PIXIZE
        jsr     AddSprite
.clrbtns
        jsr     ClearBtns
        ldx     #300        ;time delay if no btn
        stx     Delay9
        ldx     #WaitRunAct ;show cur location
        lda     #BTN_ANY
        jsr     WaitForBtn  ;wait for btn's release!

rts

PROCEND

;||||||||||||||||||||||||||||||||||||||||||||||||||
; Handle Title screen, including player interaction
;
; ENTRY:    none
;
; EXIT: none
;||||||||||||||||||||||||||||||||||||||||||||||||||

ShowTitle   PROC

.BONECHAR   =   35+(5*$400)+CHARBASE
.ERASECHAR  =   32+(0*$400)+CHARBASE

.STARTBASE  =   (19*64)+24
.OPTSBASE   =   (22*64)+24

.top
        lda     #TITLETbl
        jsr     InitBlank3      ;setup screen lda     #15
        sta     ScrnLumin If      DEBUG
        _PrintAt #mVERSION,26,4
        wai
        ENDIF lda     #INITSCORE
        sta     Score
        jsr     FadeIn ; yes!

_PlaySong #title_sng
        _APUCommand #DCOM_FADEIN,#$0101 lda     #1      ;allow demo mode to run
```

ASTHMA VIDEO GAME SOURCE CODE

```
            ldx     #.STARTBASE
            ldy     #.OPTSBASE
            jsr     TwoChoices
            lda     DemoFlag
            bfl     .cont
            lda     PlayerOne       ;save these since the
            sta     OldP1   ;demo modifies them
            lda     PlayerTwo
            sta     OldP2
            stz     PlayerTwo
.pickScript
            jsr     NewRandom
            and     #32-1   ;allows up to 32 demo scripts
            cmp     DemoScripts     ; how many scripts are there to choose from?
            bge     .pickScript asl
            tax
            lda     DemoScripts+2,x         ;select script
            sta     temp2   ; (temporary)
            lda     (temp2) ;get level #
            asl
            asl
            sta     CurLevel
            inc     temp2
            inc     temp2
            lda     (temp2) ;which team?
            sta     PlayerOne
            inc     temp2
            inc     temp2
            lda     (temp2) ;# players?
            dec
            beq     .setScripts     ;branch if only one player
            lda     PlayerOne
            clc
            adc     #4      ; else set up player two
            sta     PlayerTwo
.setScripts
            inc     temp2
            inc     temp2
            lda     (temp2) ;get player one demo script
            sta     dmscript1
            lda     PlayerTwo
            bfl     .cont
            inc     temp2
            inc     temp2
            lda     (temp2) ;get player two demo script
            sta     dmscript2
            clc             ;fool computer into playing game
.cont
            php jsr     FadeOut
            _APUCommand #DCOM_FADE_AND_STOP,#$0101
            _NewCharSet #STATUSSET,#NORMALPAL
```

Page # 8

ASTHMA VIDEO GAME SOURCE CODE

```
        plp
        bcc     .initbars;carry clear equals start game jsr     ShowOptions
        jmp     .top
.initbars
        lda     #GRNBAR
        sta     FirstBar
        lda     #VLTBAR
        sta     SecondBar lda     PlayerOne
        cmp     #4
        beq     .exit lda     #BLUBAR
        sta     FirstBar
        lda     #REDBAR
        sta     SecondBar
.exit
        rts

PROCEND
```

;[[[[[[[[[[[[[[[[[[[[[[[[[[[[[[[[[[[[[[[[[[[[[[[[[[[[[[[[[[[[
; Handle Options screen, including player interaction
;
; ENTRY:    none
;
; EXIT: none
;[[[[[[[[[[[[[[[[[[[[[[[[[[[[[[[[[[[[[[[[[[[[[[[[[[[[[[[[[[[[

```
ShowOptions     PROC

.BONECHAR   =       35+(5*$400)+CHARBASE
.ERASECHAR  =       32+(0*$400)+CHARBASE

.STARTBASE  =       (19*64)+24
.OPTSBASE   =       (22*64)+24

.top
        lda     #RECORDTbl
        jsr     InitBlank3 ldy     #0
        ldx     #768    ; set y to a 0 for screen
        jsr     FastUpdate      ; clear screen and redraw
        _NewCharSet #TRANSSET,#NORMALPAL
        wai
        lda     #grn
        ldy     #330*PIXIZE
        ldx     #200*PIXIZE
        jsr     AddSprite       ;print player 1 sprite
        lda     #blu
        ldy     #366*PIXIZE
        ldx     #200*PIXIZE
```

ASTHMA VIDEO GAME SOURCE CODE

```
        jsr     AddSprite       ;print player 2 sprite jsr     FadeIn ; yes!

_PlaySong #blank_sng
        _APUCommand #DCOM_FADEIN,#$0101 jsr     DoOptions jsr     FadeOut
        _APUCommand #DCOM_FADE_AND_STOP,#$0101
        _NewCharSet #STATUSSET,#NORMALPAL rts

PROCEND

;[[[[[[[[[[[[[[[[[[[[[[[[[[[[[[[[[[[[[[[[[[[[[[[[[[[[[
; Handle Continue screen, including player interaction
;
; ENTRY:    none
;
; EXIT: none
;[[[[[[[[[[[[[[[[[[[[[[[[[[[[[[[[[[[[[[[[[[[[[[[[[[[[[

ShowContinue  PROC

.BONECHAR   =   35+(5*$400)+CHARBASE
.ERASECHAR  =   32+(0*$400)+CHARBASE

.YESBASE    =   (16*64)+24
.NOBASE     =   (19*64)+24 lda     #STORYTbl
        jsr     InitBlank3      ;common call
        wai
        jsr     ClearBtns
        _NewCharSet #TRANSSET,#NORMALPAL
        lda     #NORMALPAL
        sta     PalType
        ldx     #4*256
        ldy     #0              ; set y to a 0 for screen
        jsr     FastUpdate      ; clear screen and redraw
        _PlaySong #title_sng
        _APUCommand #DCOM_FADEIN,#$0101
        lda     #15
        sta     ScrnLumin
        jsr     FadeIn ; yes!
.getBtn
        ;stz    DemoFlag
        lda     #0      ;disallow demomode
        ldx     #.YESBASE
        ldy     #.NOBASE
        jsr     TwoChoices
        ;if     DEMOMODE
```

ASTHMA VIDEO GAME SOURCE CODE

```
;lda    DemoFlag    ;don't allow demo mode to run
;bne    .getBtn ; during Continue screen
;endif
php
jsr     FadeOut
_APUCommand #DCOM_FADE_AND_STOP,#$0101
_NewCharSet #STATUSSET,#NORMALPAL plp
rts PROCEND
;IIIIIIIIIIIIIIIIIIIIIIIIIIIIIIIIIIIIIIIIIIIIIIIII
; Handle screens with 2 choices
;
; ENTRY:    A = 0=don't allow demo mode, 1=turn on demo mode
;           X = first position for pointer
;           Y = second position
;
; NOTE: character #32 (space) is used to clear pointer character
;       and pointer is assumed to be two characters wide
;
; EXIT: clc = top choice selected
;       sec = bottom selected
;IIIIIIIIIIIIIIIIIIIIIIIIIIIIIIIIIIIIIIIIIIIIIIIII TwoChoices   PROC

.BONECHAR   =   35+(5*$400)+CHARBASE
.ERASECHAR  =   32+(0*$400)+CHARBASE

.STARTBASE  =   (19*64)+24
.OPTSBASE   =   (22*64)+24 wai
        sta     temp3
        stx     temp8
        sty     temp8+2 jsr     ClearBtns
        _NewCharSet #TRANSSET,#NORMALPAL    ;reset screen's appearance
        wai .btnup
        stz     temp3+2 ldx     temp8
        lda     #.BONECHAR
        sta     >SCRN3RAM_B,x
        inc
        inx
        inx                 ;next position, same character
        sta     >SCRN3RAM_B,x ldx     temp8+2
```

Page # 11

ASTHMA VIDEO GAME SOURCE CODE

```
        lda     #.ERASECHAR
        sta     >SCRN3RAM_B,x
        inx
        inx             ;next position, same character
        sta     >SCRN3RAM_B,x ;ÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄ
.event
        inc     Update3         ;force update
.loop
        lda     temp3
        beq     .noDem
        ldx     #200    ;time delay if no btn
        stx     Delay9
        ldx     #WaitDelay
        lda     #BTN_ANY
        jsr     WaitForBtn
        btr     .chkBtn ;branch if user pressed button
        inc     DemoFlag        ; else begin demo mode
        rts
.noDem
        ldx     #750    ;on some screens demo mode is not wanted
        stx     Delay9
        ldx     #WaitDelay
        lda     #BTN_ANY
        jsr     WaitForBtn
        bne     .chkBtn
        sec             ;if time runs out, second choice is forced
        rts
.chkBtn
        cmp     #BTN_START      ;start selects choice
        beq     .btnst
        cmp     #BTN_UP         ;move pointer up
        beq     .btnup
        cmp     #BTN_DN         ;move pointer down
        beq     .btndn
        bra     .loop
;ÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄ
.btndn
        sta     temp3+2 ldx     temp8
        lda     #.ERASECHAR
        sta     >SCRN3RAM_B,x
        inx
        inx             ;next position, same character
        sta     >SCRN3RAM_B,x ldx     temp8+2
        lda     #.BONECHAR
        sta     >SCRN3RAM_B,x
        inc
        inx
        inx             ;next position, same character
        sta     >SCRN3RAM_B,x
        bra     .event
```

Page # 12

ASTHMA VIDEO GAME SOURCE CODE

```
;ÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄ
.binst
        clc                     ;clc = first choice selected
        lda     temp3+2
        beq     .ret
        sec                     ;sec = second choice
.ret
        rts

PROCEND

;ÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄ
; add player sprite to screen using PlayerTbl
;
; ENTRY:        A = player # (0 = none, 1*4 = grn, 2*4 = red)
;       Y = actor type
;
; EXIT: X = PlayerID#

AddPlayer
        phy                     ;save player type lsr
        tax
        and     #2              ;player one has bit one set
        tay lda     PlayerTbl-2,x   ;get script addr.

ldx     #DUDEX
        cpy     #2
        beq     .cont
        ldx     #DUDEX+1024
.cont
        ldy     #DUDEY
        jsr     AddSprite       ;start sprite going ldx     temp    ;return w/X=sprite index
        pla             ; Get PLAYERONE/PLAYERTWO
        sta     SprType,x       ; & w/type set appr.
        tax
        lda     SetPeak1,x
        sta     Peakflow1,x
        lda     SetCold1,x
        sta     Cold1,x
        jsr     SetupRecord
        jsr     InitAsRecord
        jsr     AdjustRecord
;       lda     temp ldx     temp    ;return w/X=sprite index
        RTS
        PROCEND ;IIIIIIIIIIIIIIIIIIIIIIIIIIIIIIIIIIIIIIIIIIIIIIIIIIIII
; *** NOTE: this version just adds any monsters on the screen!
```

ASTHMA VIDEO GAME SOURCE CODE

```
; ENTRY:     screen record in DP setup (data ptrs, sizes, position info)
;
; EXIT: NONE
;
; (LAI)
;IIIIIIIIIIIIIIIIIIIIIIIIIIIIIIIIIIIIIIIIIIIIIIIIIIIIIIIIIII NewDisplay   PROC lda     VPosition
        sec             ;Compute starting Y value (left edge of display - 1 character).
        sbc     #CHRSIZE
        bcs     .ud1    ;Don't go past top.
        lda     #0
.ud1
        tay
        lda     VPosition
        clc             ;Compute ending Y value (right edge of display + 1 character).
        adc     #224+CHRSIZE
        pha
.udloop
        stz     MonType ;assume no monster in row phy             ;Save current Y.
        tya
        ldx     #0
        jsr     UpdateRow       ;Draw an entire row of characters.
        stz     VFlag
        stz     HFlag   ;*** no need to DMA (it's already there!)

ldy     MonType ;check monster flag
        beq     .noscrl jsr     AddMonster      ;with info in buffers...
        stz     MonType
.noscrl
        pla
        clc
        adc     #CHRSIZE        ;next
        tay
        cmp     1,S     ;Until we reach the end.
        blt     .udloop pla             ;clean up stack jmp     RunActors

PROCEND

;IIIIIIIIIIIIIIIIIIIIIIIIIIIIIIIIIIIIIIIIIIIIIIIIIIIIIIIIIII
; Check for control buttons (pause, restart, etc...)

CheckBtns    PROC ldy     DemoFlag
```

Page # 14

ASTHMA VIDEO GAME SOURCE CODE

```
        bfl     .begin
        rts
.begin
        ldy     #BTN_NONE
        tyx lda     DeathFlag       ;if P1 dies, disable his joystick
        cmp     PlayerID1
        beq     .chkP2 ldy     JOY1_S
        ;tay
        cpy     #BTN_SELECT ;inventory?
        bne     .chkP2 lda     PlayerOne
        ldy     #PLAYERONE
        jmp     AsthmaScreen
        ;jsr    AsthmaScreen
        ;rts
.chkP2
        lda     PlayerTwo       ;don't try player2 if only 1 player
        beq     .chkSt lda     DeathFlag       ;if P2 dies, make him impotent
        cmp     PlayerID2
        beq     .chkSt ldx     JOY2_S
        cpx     #BTN_SELECT ;inventory?
        bne     .chkSt ;lda    PlayerTwo
        ldy     #PLAYERTWO
        jmp     AsthmaScreen
;AAAAAAAAAAAAAAAAAAAAAAAAAAAAAAAAAAAAAAAAAAAAAAAAAAAAAAAAAAA
.chkSt
        tya
        cmp     #BTN_START  ;pause by player one?
        beq     .doSt txa
        cmp     #BTN_START  ;pause by player two?
        beq     .doSt rts
.doSt
        _WinText #mPause jsr     Wait4Null
.nobs
        lda     #BTN_ANY
        jsr     Wait4Null       ;show paused cmp     #BTN_START  ;restart level?
        beq     .unpause
```

```
            IFNOT   CHEAT ;000
            bra     .nobs
            else
;           pha
;           jsr     CLS2
;           pla
.nobx
;           cmp     #BTN_SELECT ;reset?
;           bne     .nobl
;           jmp     Restart
.nobl
;           cmp     #BTN_A       ;skip four levels forward
;           bne     .by
;           lda     CurLevel
;           clc
;           adc     #12
;           cmp     LevelMax
;           bge     .br
;           bra     .aok
.by
            cmp     #BTN_Y       ;skip four levels backward
            bne     .bnr
;           lda     CurLevel
;           sec
;           sbc     #20
;           bpl     .aok
;           lda     #0
;           bra     .aok
.bnr
            cmp     #BTN_R       ;next level?
            bne     .nor lda     CurLevel
            bit     #%00001100   ;check for boss level
            btr     .br
            dec     WhichBoss
            cmp     #100    ;is this Rex level?
            bne     .br
            dec     WhichBoss
            bra     .br
.nor
            cmp     #BTN_L       ;prev lev?
            bne     .bd lda     CurLevel
            sec
            sbc     #8      ; yes- just restart next!
            bpl     .aok
            lda     LevelMax
            sec
            sbc     #8
.aok
            sta     CurLevel
            tax
```

SOURCE CODE

```
        .br
                }
                rts
                ;bra
        .sl
                lda     #-1
                sta     DeathFlag
        .bd
                bra     .nobs
;               RTS
                endif
        .unpause
                jmp     CLS2

PROCEND
;[[[[[[[[[[[[[[[[[[[[[[[[[[[[[[[[[[[[[[[[[[[[[[[[[[
; Add to player's score
;
;       Enter: A= low word
;              X= high word AddScore        PROC .normal
                sed
                clc
                adc     Score
                sta     Score
                php
                bcs     .ExLife
                txa
                beq     .HiWord .ExLife
                phx
                jsr     Add1Live
                _PlayEffect #pickup_eff
                plx .HiWord
                txa
                plp
                adc     Score+2
                sta     Score+2
                cld
.done2
                RTS PROCEND
;[[[[[[[[[[[[[[[[[[[[[[[[[[[[[[[[[[[[[[[[[[[[[[[[[[
; Add 1 extra live 2 each player if they
; are still alive
;[[[[[[[[[[[[[[[[[[[[[[[[[[[[[[[[[[[[[[[[[[[[[[[[[[
```

ASTHMA VIDEO GAME SOURCE CODE

```
Add1Live     PROC
             ldy      Lives1   ;extra life every 10,000 points
             cpy      #MAXLIVES
             bge      .chkp2
             inc      Lives1
.chkp2
             ldy      PlayerTwo
             beq      .done
             ldy      Lives2
             cpy      #MAXLIVES
             bge      .done
             inc      Lives2
.done
             rts
             PROCEND
;IIIIIIIIIIIIIIIIIIIIIIIIIIIIIIIIIIIIIIIIIIIIIIIIII
;
; Show various single screens, requiring no Sprs or any
; other action other than: init, show, wait 4 btn, hide
;
;IIIIIIIIIIIIIIIIIIIIIIIIIIIIIIIIIIIIIIIIIIIIIIIIII
;AAAAAAAAAAAAAAAAAAAAAAAAAAAAAAAAAAAAAAAAAAAAAAAAAAAAAAAA
ShowBonus PROC .BBSTART     =        (15*64)+42
.BBLASTL     =        11+(6*$400)+CHARBASE
.BBLASTR     =        12+(6*$400)+CHARBASE ;            jsr      FadeOut
             lda      #STAGETbl
             jsr      InitBlank3        ;common call
             _NewCharSet #TRANSSET,#NORMALPAL      ;reset screen's appearance sed
             lda      #$5
             sta      BonusP
             lda      PlayerTwo    ; Cmp to see if 2 players
             beq      .oneP    ; If skip to do rest of bonus stuff
             lda      #$8
             sta      BonusP
.oneP
             cld
             stz      BonusB; Zero the asthma running bonus
             lda      #PF1Lo; Get lo peakflow pointer in A
             sta      temp3+2      ; Store pointer in temp3+2
             lda      CurLevel     ; Get Current level
             lsr               ; Shift right ( /2)
             dec              ; Dec twice to get 1,2,3,4,5,etc
             dec
             tay              ; Put level # in Y
             lda      (temp3+2),y    ; Use pointer indexed by level to get PF
             sed
             sta      BonusB
             cmp      #$7
             blt      .nobo
             cmp      #$9
```

ASTHMA VIDEO GAME SOURCE CODE

```
              blt     .chkp2
              lda     #$1
              sta     temp3
              jsr     .ChkPerf
              bra     .chkp2
.nobo
              stz     BonusB
.chkp2
              lda     PlayerTwo       ; Cmp to see if 2 players
              beq     .cont           ; If skip to do rest of bonus stuff
              ldx     #PF2Lo          ; Get player two's low PF point
              stx     temp3+2         ; Store pointer in temp3+2
              lda     (temp3+2),y     ; Use pointer indexed by level to get PF
              tax
              cmp     #$7
              blt     .no2bo
              cmp     #$9
              blt     .tally
              lda     #$1
              sta     temp3
              jsr     .ChkPerf
              bra     .tally
.no2bo
              ldx     #$0
.tally
              txa
              clc
              adc     BonusB
              sta     BonusB
.cont
              lda     BonusB
              jsr     .mult100
              sta     BonusB lda     BonusA          ; Get pickup bonus
              sta     temp3
              jsr     .ChkPerf
              jsr     .mult100        ; Multiply by 100
              sta     BonusA          ; Save value
              clc
              adc     BonusA          ; and add to itself for X 200 bonus
              sta     BonusA          ; Save value lda     BonusE          ; Get Question Bonus
              sta     temp3
              jsr     .ChkPerf
              jsr     .mult100        ; Multiply it by 100
              sta     BonusE          ; Save value
              sta     BackA           ; Save X by 100 value
              clc
              adc     BonusE          ; and add to itself for X 200 bonus
              sta     BonusE
              clc
              adc     BonusE          ; add to itself again for X 400 bonus
              clc
              adc     BackA           ; add X 100 to X 400 for X 500 bonus
```

ASTHMA VIDEO GAME SOURCE CODE

```
            sta     BonusE ; Save final Bonus value
            clc
            adc     BonusB
            clc
            adc     BonusA
            sta     BonusT
            cld
            _PrintAt #mBonusTitle,3,3
            _PrintAt #mBonusA,6,3
            _PrintAt #mBonusB,8,3
            _PrintAt #mBonusE,10,3
            _PrintAt #mBonusT,12,3
            jsr     PutPlayers
            jsr     FadeIn
            lda     BonusA
            ldx     #((6)*64)+(48)
            jsr     .NumCount
            lda     BonusB
            ldx     #((8)*64)+(48)
            jsr     .NumCount
            lda     BonusE
            ldx     #((10)*64)+(48)
            jsr     .NumCount
            lda     BonusT
            ldx     #2*$400
            stx     temp8
            ldx     #((12)*64)+(48)
            jsr     PrintNum
            ldx     #0
            lda     BonusT
            jsr     AddScore .chkBBlast
            lda     BonusQ
            bne     .waitD
            _PrintAt #mBonusQ,15,3
            ldy     #5
            sty     BackY
            ldx     #.BBSTART
            stx     BackX
.Loop
            ldx     BackX
            lda     #.BBLASTL
            sta     >SCRN3RAM_B,x
            inx
            inx
            lda     #.BBLASTR
            sta     >SCRN3RAM_B,x
            inx
            inx
            stx     BackX
            inc     Update3
            lda     Weapon1
            cmp     #99
            bge     .incp2bb
            inc     Weapon1
```

ASTHMA VIDEO GAME SOURCE CODE

```
.incp2bb
        lda     PlayerTwo       ; Cmp to see if 2 players
        beq     .CLoop  ; If skip to do rest of bonus stuff
        lda     Weapon2
        cmp     #99
        bge     .CLoop
        inc     Weapon2
.CLoop
        dec     BackY
        beq     .waitD
        ldx     #25     ; time delay if no btn
.del
        wai
        dex
        bne     .del
        bra     .Loop
.waitD
        lda     BonusP
        bne     .pressw
        _PrintAt #mBonusP,17,3
        jsr     Add1Live
        lda     #ExtraLifeScript
        ldx     #190*PIXIZE
        ldy     #150*PIXIZE
        jsr     AddSprite
.pressw
        ldx     #265    ; time delay if no btn
        stx     Delay9
        lda     #BTN_ANY
        ldx     #WaitRunAct
        jsr     WaitForBtn
        rts
;ÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄ
.mult100
        asl
        asl
        asl
        asl
        asl
        asl
        asl
        asl
        rts
;ÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄ
.NumCount
        stx     BackX
        sta     BackA
        lda     #$0
        sta     BackY
.loop
        sed
        lda     BackY
        cmp     BackA
        beq     .ret
        clc
        adc     #$10
```

Page # 21

ASTHMA VIDEO GAME SOURCE CODE

```
        sta     BackY
        jsr     .ret
        wai
        bra     .loop ;ÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄ
.ret
        ldx     #5*$400
        stx     temp8
        ldx     BackX
        jsr     PrintNum
        inc     Update3
        _PlayEffect #button_eff
        cld
        rts ;ÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄ
.ChkPerf
        sta     BackA
        lda     BonusP
        sec
        sbc     temp3
        sta     BonusP
        lda     BackA
        rts
        PROCEND
;ÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄ
PutPlayers   PROC
        lda     PlayerOne
        sec
        sbc     #4
        lsr
        lsr
        tax
        lda     .SSpriteTbl,x
        ldx     #60*PIXIZE
        ldy     #200*PIXIZE
        jsr     AddSprite
        jsr     RunActors       ;keep actors acting
        rts .SSpriteTbl
        dw      BronkieINTScript,TrakieINTScript
        PROCEND
;ÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄ
ShowDisclaimer PROC jsr     FossilScreen
        _PrintAt #mDisclaimer,6,4
        jsr     FadeIn ldx     #400    ;time delay if no btn
        stx     Delay9
        ldx     #WaitDelay
        lda     #BTN_ANY
        jsr     WaitForBtn
```

ASTHMA VIDEO GAME SOURCE CODE

```
        jmp     FadeOut

PROCEND

;ÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄ
ShowLogos   PROC

_InitMusic          ;upload & init music driver
        lda     #LOGOSTbl
        jsr     InitBlank3      ;common call
        _NewCharSet #TRANSSET,#NORMALPAL    ;reset screen's appearance
        _PrintAt #mLicense,2,6
        lda     #100
        sta     MachineSeq
        sta     MachStat
        lda     #-1
        sta     temp8+2
        lda     #2800
        sta     Delay9
        lda     #200    ;time delay
        sta     temp8
        ldx     #166*PIXIZE
        ldy     #137*PIXIZE
        jsr     MoveBGScreen
        jmp     FadeOut         ;turn off music and fade to black
        PROCEND ;ÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄ
ShowWQ      PROC
.wave
        lda     #72
        sta     MachineSeq
        stz     MachStat
        stz     MachStat
        lda     #WQTbl
        jsr     InitBlank3      ;setup screen
        lda     #-2
        sta     temp8+2
        lda     #600    ; delay between each move
        sta     Delay9
        lda     #130    ; delay till scene is over
        sta     temp8
        ldx     #218*PIXIZE
        ldy     #189*PIXIZE
        jsr     MoveBGScreen
        jmp     endshow         ;turn off music and fade to black MoveBGScreen lda     #SparkleScript
        jsr     AddSprite
        jsr     FadeIn  ; yes!

;scroll paralax until joy pressed, or time passes jsr     SetBG2
```

ASTHMA VIDEO GAME SOURCE CODE

```
        jsr     ClearBtns
.loop wai
.nom lda     temp8+2         ;12 bit scroll
.h4
        sta     HScrollSpd
.h3
        lda     VConstSpd       ;always moving?
        sta     VScrollSpd
.v3
        jsr     DoScroll        ;scroll the paralax stz     MoveV
        stz     MoveH ldy     Delay9
.lup
        dey
        bne     .lup wai
        lda     MachStat
        bne     .wayhere
        lda     JOY1_S
        bne     .exit lda     JOY2_S
        bne     .exit
        bra     .normal
.wayhere
        dec     MachStat
.normal
        lda     MachineSeq
        beq     .moveact
        dec     MachineSeq
.moveact
        jsr     RunActors
        dec     temp8   ;stop if reached end of time
        bne     .loop
.exit
        stz     MachineSeq
        rts

PROCEND
```

;IIIIIIIIIIIIIIIIIIIIIIIIIIIIIIIIIIIIIIIIIIIIIIIIIIIIIIIII
; Handle the Record screen, including player interaction Page # 24

ASTHMA VIDEO GAME SOURCE CODE

```
;
; ENTRY:    A = playerID1
;           Y = player equate (PLAYERONE or PLAYERTWO)
;
; EXIT: none
;IIIIIIIIIIIIIIIIIIIIIIIIIIIIIIIIIIIIIIIIIIIIIIIIIIIIII ShowAsthmaRecord    PROC lda     #15
        sta     ScmLumin _PlaySong #asthma_sng
        _APUCommand #DCOM_FADEIN,#$0101 ldx     Lives1
        beq     .chkP2 lda     PlayerOne
        sta     CurPlayer       ;CurPlayer = PlayerOne or PlayerTwo jsr     .DoIt .chkP2
        lda     PlayerTwo
        bfl     .xit        ;branch if single player game sta     CurPlayer       ;CurPlayer = PlayerOne or PlayerTwo
        ldx     Lives2
        beq     .xit .DoIt
        lda     #RECORDTbl
        jsr     InitBlank3 ldy     #0
        ldx     #256    ; set y to a 0 for screen
        jsr     FastUpdate  ; clear screen and redraw
        _NewCharSet #TRANSSET,#NORMALPAL
        _PrintAt #mAsthmaRecText,7,4
        lda     CurPlayer
        lsr
        tax
        stz     PlayHit1
        stz     PlayHit2
        lda     Psprtbl,x
        ldx     #230*PIXIZE
        ldy     #210*PIXIZE
        jsr     AddSprite
        jsr     RunActors
        jsr     DoAsthmaRecord      ; New asthma record proc. old=FillInRecord
        inc     Update3     ; force update
        wai
        jsr     FadeIn
```

ASTHMA VIDEO GAME SOURCE CODE

```
        jsr     ClearBtns ldx     #300        ;time delay if no btn
        stx     Delay9
        ldx     #WaitRunAct ;show cur location
        lda     #BTN_START
        jsr     WaitForRightBtn
        jsr     FadeOut
xit
        rts

PROCEND
```

;||||||||||||||||||||||||||||||||||||||||||||||||||||||
; Handle the Record screen, including player interaction
;
; ENTRY:    A = playerID1
;           Y = player equate (PLAYERONE or PLAYERTWO)
;
; EXIT: none
;||||||||||||||||||||||||||||||||||||||||||||||||||||||

ShowDailyMedsPROC

```
        lda     #15
        sta     ScmLumin
        lda     #RECORDTbl
        jsr     InitBlank3 ldy     #0
        ldx     #512        ; set y to a 0 for screen
        jsr     FastUpdate  ; clear screen and redraw
        _PlaySong #title_sng
        _APUCommand #DCOM_FADEIN,#$0101
        wai
        _NewCharSet #TRANSSET,#NORMALPAL
        lda     #DailyMedScript
        ldx     #215*PIXIZE
        ldy     #208*PIXIZE
        jsr     AddSprite
        jsr     RunActors
        jsr     RunActors
        lda     CurLevel
        sec
        sbc     #4          ; Fact # already *4 so need to subtract 4
        asl                 ; then *4 again since questions are spaced
        sta     temp8
        lda     #mFact1A1
        clc
        adc     temp8
        tay
        ldx     #((17)*256)+(4) ;#(\top*256)+\lft
        jsr     PrintAt
        jsr     FadeIn
        stz     BackA
        stz     temp8
```

Page # 26

ASTHMA VIDEO GAME SOURCE CODE

```
        stz     MachineSeq
.loop
        lda     #mInhalerU1
        clc
        adc     temp8
        tay
        ldx     #((15)*256)+(6)  ;#(\top*256)+\lft
        jsr     PrintAt
.waitseq
        ldx     #5
        stx     Delay9
        ldx     #WaitRunAct     ;show cur location
        lda     #BTN_START
        jsr     WaitForBtn      ;wait for btn's release!
        If      CHEAT
        bne     .done           ;uncomment to skip Dmeds @ anytime
        ENDIF
        beq     .cont
        lda     BeenThere
        cmp     CurLevel
        beq     .done
        lda     CurLevel
        and     #%00001100
        cmp     #%00000100
        bne     .done
.cont
        lda     MachineSeq
        cmp     BackA
        beq     .waitseq
        sta     BackA
        lda     temp8
        clc
        adc     #4
        sta     temp8
        lda     MachineSeq
        cmp     #7
        blt     .loop
        jsr     ClearBtns ldx     #WaitRunAct     ;show cur location
        lda     #BTN_ANY
        jsr     WaitForBtn      ;wait for btn's release!
.done
        lda     CurLevel
        sta     BeenThere
        jmp     endshow         ;turn off music and fade to black

PROCEND

;ÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄ
ShowLevelIntro PROC lda     #15
        sta     ScrnLumin
```

ASTHMA VIDEO GAME SOURCE CODE

```
        lda     #INTROTbl
        jsr     InitBlank3      ;setup screen
        _NewCharSet #TRANSSET,#NORMALPAL lda     CurLevel
        lsr                     ;modify CurLevel to point to appropriate intro screen
        lsr
        dec
        pha                     ;save for adding sprites
        lsr
        lsr
        inc
        xba                     ;multiply by 256 tax
        ldy     #0
        jsr     FastUpdate      ;setup level screen lda     1,s
        inc
        cmp     #25     ; Is this the REXO boss level?
        beq     .doBoss         ; Yes then dont do trigger stuff
        bit     #3      ; Boss level?
        beq     .doBoss
                                ; print screen text
        _PrintAt #mTrigWarn,11,2        ; y,x print warning message
        lda     1,s
        cmp     #3
        bit     .addSprs
        _PrintAt #mGetPiece,22,2        ; y,x print machine piece text
        bra     .addSprs
.doBoss
        ldx     #7*256
        stx     BossINT
        ldy     #0
        jsr     FastUpdate      ;setup boss screen ;add sprites
.addSprs
        pla
        asl
        asl
        pha                     ;save for adding actors
        clc
        adc     #mTrigDesc      ;print trigger descriptions
        tay
        ldx     #(4*256)+3      ;was 17*256
        jsr     PrintAt pla
        asl
        sta     temp8
        asl
        clc
        adc     temp8   ;multiply by 24
        tax
```

ASTHMA VIDEO GAME SOURCE CODE

```
        ldy     #4          ;allows four actors for non-boss levels
        lda     CurLevel
        cmp     #100
        bfl     .rexo
        and     #%00001100  ;check for non-boss level
        btr     .st
.rexo
        ldy     #2          ;just 2 sprites for boss levels lda     PlayerOne
        cmp     #4          ;check for team bronkie
        beq     .st txa
        clc
        adc     #12         ;set x for team trakie
        tax
.st
        sty     temp8
.loop
        lda     LevelIntroTbl,x  ;push x value to stack
        pha
        inx
        inx lda     LevelIntroTbl,x  ;transfer y value
        tay
        inx
        inx lda     LevelIntroTbl,x  ;get script address
        stx     temp8+2
        plx                      ;pull x
        jsr     AddSprite ldx     temp8+2     ;get x for next iteration
        inx
        inx
        dec     temp8       ;are we through?
        bne     .loop _PlaySong #asthma_sng
        _APUCommand #DCOM_FADEIN,#$0101 jsr     FadeIn      ; yes!

jsr     ClearBtns
        ldx     #265
        stx     Delay9
        ldx     #WaitRunAct ;show cur location
        lda     #BTN_ANY
        jsr     WaitForBtn  ;wait for btn's release!
        stz     BossINT jsr     endshow     ;turn off music and fade to black
```

ASTHMA VIDEO GAME SOURCE CODE

```
        jmp     SetLuminance    ; then set luminance for fade in

PROCEND

;ÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄ
ShowStory   PROC .telltale
        lda     #STORYTbl
        jsr     InitBlank3      ;setup screen _NewCharSet #TRANSSET,#NORMALPAL
        _PrintAt #mIntro1Msg,11,2    ;y,x _PlaySong #bossa_sng
        _APUCommand #DCOM_FADEIN,#$0101 jsr     FadeIn  ; yes!

jsr     ClearBtns lda     #3              ; set # of text Msgs
        sta     temp8           ; Store in temp 8
        lda     #mIntro2Msg     ; get Address of first Msg
        sta     temp8+2         ; store in temp 8+2
        lda     #256            ; set first screen offset
        pha                     ; push it onto the stack .loop
        ldx     #500            ; time delay if no btn
        stx     Delay9
        ldx     #WaitDelay
        lda     #BTN_ANY
        jsr     WaitForBtn lda     1,S             ; get x screen pointr off stack
        tax                     ; without disrupting it
        ldy     #0              ; set y to a 0 for screen
        jsr     FastUpdate      ; clear screen and redraw lda     temp8+2         ; get pointer to Msg
        tay                     ; \str
        clc
        adc     #4              ; Increment to next Msg
        sta     temp8+2         ; Put it back in temp 8+2
        ldx     #(11*256)+2     ; #(\top*256)+\lft
        jsr     PrintAt ; print the next msg pla                     ; get x position from stack
        clc
        adc     #256            ; set to next screen
        pha                     ; push it back onto stack
```

ASTHMA VIDEO GAME SOURCE CODE

```
        dec     temp8   ; decrement counter
        bne     .loop
        pla ldx     #500    ; time delay if no btn
        stx     Delay9
        ldx     #WaitDelay
        lda     #BTN_ANY
        jsr     WaitForBtn jmp     endshow         ;turn off music and fade to black

PROCEND

;ÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄ
ShowVictory     PROC lda     #VICTORYTbl
        ldy     #victory_sng    ;Replaced with boss music till then
        jsr     ShowScreen jsr     ClearBtns
        stz     MachineSeq
        lda     #VictoryScript
        ldx     #215*PIXIZE
        ldy     #208*PIXIZE
        jsr     AddSprite
        ldx     #500    ;time delay if no btn
        stx     Delay9
        ldx     #WaitRunAct     ;show cur location
        lda     #BTN_ANY
        jsr     WaitForBtn      ;wait for btn's release!
        _APUCommand #DCOM_FADE_AND_STOP,#$0101
        jsr     FadeOut
        jsr     ShowCredits2
;       jsr     ShowCredits
        jmp     endshow         ;turn off music and fade to black

PROCEND

;ÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄ
ShowMachineScm  PROC lda     #15
        sta     ScmLumin
        lda     #MACHUPTbl
        ldy     #asthma_sng
        jsr     ShowScreen
        jsr     ClearBtns
        rts

PROCEND

;ÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄ
ShowCredits2 PROC
```

ASTHMA VIDEO GAME SOURCE CODE

```
        lda     #STAGETbl
        jsr     InitBlank3      ;common call
        _NewCharSet #TRANSSET,#NORMALPAL
        lda     #10
        sta     MachineSeq
        lda     #15
        sta     ScmLumin
        jsr     FadeIn
        bra     DoCredits
;ÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄ
ShowCredits PROC jsr     FossilScreen
        stz     MachineSeq
DoCredits
        lda     #6
        sta     BackA
        stz     BackX
        stz     BackY .PrintCredits
        jsr     CLS
        lda     BackY
        clc
        adc     #mCredit
        tay
        ldx     #(4*256)
        wai
        jsr     PrintAt
        lda     MachineSeq
        bne     .nexttext
        jsr     FadeIn
.nexttext
        inc     BackY
        inc     BackY
        inc     BackY
        inc     BackY
        ldx     #400
        stx     Delay9
        lda     #BTN_ANY
        ldx     #WaitRunAct
        jsr     WaitForBtn
        dec     BackA
        beq     .Donehere
        lda     MachineSeq
        bne     .PrintCredits
        jsr     FadeOut
.nofade
        bra     .PrintCredits
.Donehere
        lda     MachineSeq
        bne     .tdone
        jsr     FadeOut
.tdone
        rts
```

Page # 32

ASTHMA VIDEO GAME SOURCE CODE

```
        PROCEND
;ÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄ
FossilScreen   PROC
        lda     #STORYTbl
        jsr     InitBlank3      ;common call
        wai
        jsr     ClearBtns
        _NewCharSet #TRANSSET,#NORMALPAL
        ldx     #6*256
        ldy     #0              ; set y to a 0 for screen
        jsr     FastUpdate      ; clear screen and redraw
        lda     #15
        sta     ScrnLumin
        rts

PROCEND

;ÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄ
;DoScreen       PROC    ;REQURES A,X = ptr to screen table
;
;       jsr     ShowScreen      ;show it!
;
;       jsr     Wait4Null
;
;       _APUCommand #DCOM_FADE_AND_STOP,#$0101
;
;       jmp     FadeOut
;
;       PROCEND
;
;ÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄ
; Used to show information screens InitBlank3      PROC pha
        jsr     InitSprites
        pla ldx     #^SCRN3Tbl
        ldy     #SCRN3Tbl
        jsr     InitMode1       ;init screens jmp     ScreenWin       ; & window

PROCEND

;ÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄÄ
endwait PROC
        lda     #BTN_ANY
        jsr     Wait4Null
```

ASTHMA VIDEO GAME SOURCE CODE

```
endshow
        _APUCommand #DCOM_FADE_AND_STOP,#$0101
        jmp     FadeOut
        PROCEND
;//////////////////////////////////////////////////
; Startup code. This gets called whenever the RESET line on the 65816
; is pulled. (ie, power-on, reset button). Must initialize & startup game
;
; ENTRY:    NONE
;
; EXIT: NONE
;//////////////////////////////////////////////////
Start   PROC sei
        cld             ;put the CPU in a known mode clc
        xce             ;Turn on native mode.
        LAl lda     #STACKEND
        tcs             ;Set the stack pointer.

lda     #ZPAGE/256   ;Set the direct page register.
        tad lda     #DATA_PAGE
        pha
        plb
        plb             ;Set the data page register.

cli jsr     InitSNES    ;Set PPU registers and clear V-RAM.

_InitMusic      ;upload & init music driver lda     #SPRITEPAL
        ldx     #^SPRITEPAL
        sta     SprPalette      ;let Spr handler know where the palette is
        stx     SprPalette+2 lda     #1      ;set screen wrapping mode
        sta     ScmWrap lda     #15     ;initialize screen luminescence
        sta     ScmLumin _Language #lEnglish     ;set correct language
```

ASTHMA VIDEO GAME SOURCE CODE

```
            ;lda    #sInfoSize      ;ensure InitSprites normal clear
            ;sta    mInfoSize ;jsr    ShowLicense     ;show nintendo they own us
            jsr     ShowLogos       ;show everybody their piece of us jsr     Randomize       ;insure random #s usable if      RAYA
            jsr     ShowWQ jsr     ShowDisclaimer  ;inform everyone we don't advocate any of this
            endif lda     #4              ;this needs to be set before ShowTitle
            sta     PlayerOne
            stz     PlayerTwo       ;assume a single player
            stz     PalType
            dec     PalType DemoLoop
            lda     #4     ;100     ;this needs to be set before ShowTitle
            sta     CurLevel        ;Slevel
            stz     dmcount1
            stz     dmcount2
            stz     PlayHit1        ;nobody's hit!
            stz     PlayHit2
            jsr     ShowTitle       ;display our creation
            lda     DemoFlag
            bne     .noStory if      STORY
            jsr     ShowStory
            endif
.noStory if      DEBUG
            lda     JOY1_S
            btr     Main
            endif ;           jsr     ShowRaya        ;show raya screen
            bra     Main
Restart
            jsr     FadeOut          ;hide license screen!

PROCEND
```

;!!!!!!!!!!!!!!!!!!!!!!!!!!!!!!!!!!!!!!!!!!!!!!!!!!!!!
; This is the main game loop. It checks for all of the
; things we need to do and keeps the screen and Sprs updated.
;
; ENTRY:    NONE
;

ASTHMA VIDEO GAME SOURCE CODE

```
; EXIT: NONE
;
; (LAI)
;///////////////////////////////////////////

Main    PROC stz     VBFlag
        stz     SpriteFlag      ;init update variables
        stz     VFlag
        stz     HFlag
;       stz     Stars
        stz     GetAClue lda     #CONTINUES      ;init max continues per game
        sta     Continues jsr     InitPlayers
Retry
        _NewCharSet #STATUSSET,#NORMALPAL ldx     CurLevel
LevelLoop
        stz     MoveH   ;insure no world/sprite movement!
        stz     MoveV stz     xmove   ;insure not carried over to
        stz     ymove   ; map sprite.

jsr     DoMap
SetLevel
        stx     CurLevel        ;allow user to choose level stz     DoneFlag
        stz     DeathFlag
        lda     PlayerTwo       ;if 2 player game, set DeathFlag
        bfl     .cont1  ;if one of the players has lost
        lda     Lives1  ;all his lives
        btr     .chk2
        lda     PlayerID1
        bra     .setDF
.chk2
        lda     Lives2
        btr     .cont1
        lda     PlayerID2
.setDF
        sta     DeathFlag
.cont1
        stz     VBFlag
        stz     SpriteFlag      ;init update variables
        stz     VFlag
        stz     HFlag
        stz     PlayHit1        ;nobody's hit!
        stz     PlayHit2
        stz     TrigHit1        ;nobody's triggered
        stz     TrigHit2
```

Page # 36

ASTHMA VIDEO GAME SOURCE CODE

```
            stz     NumRight
            stz     SprGotHit+$3E  ;so player gets asked question only once
            stz     SprGotHit+$3C
            stz     MachineSeq
            stz     HelperFlag
            stz     FrankFlag
            stz     BonusE
            stz     BonusA
            stz     BonusB
            stz     BonusQ
            stz     BossINT
            stz     GetAClue
            ldy     #0
            lda     PlayerTwo
            bne     .no2player
            iny
.no2player
            sty     PInhal
            sty     PRxpac
            inc     MachStat lda     DemoFlag
            bne     .noIntro lda     CurLevel
            and     #%00001100     ;check for non-boss level
            bfl     .doIntro
            lda     CurLevel
            cmp     #100
            beq     .doIntro if      DAILYMED
            jsr     ShowDailyMeds; Do Daily Meds screen stuff
            endif
.doIntro
            if      LVLINT
            jsr     ShowLevelIntro ;show them what they need and need to avoid
            endif
.noIntro
            jsr     SetLuminance   ;set screen luminance based on peakflow levels
            ldx     CurLevel
            jsr     GameLoop lda     DemoFlag       ;check if demo running
            bfl     .contChk
            stz     DemoFlag       ;demo just ended, return to start (title) screen
            lda     OldP1
            sta     PlayerOne
            lda     OldP2
            sta     PlayerTwo
            jmp     DemoLoop
.contChk
            lda     DeathFlag      ;died?
            beq     .ok    ;no, go to next level
            bmi     .allDead       ;have all players died?
```

ASTHMA VIDEO GAME SOURCE CODE

```
            cmp     PlayerID1       ;one player survived
            bne     .decP2
            lda     Lives1  ;dec P1's lives if any remain
            bfl     .ok
            dec     Lives1  ;player 2 did so dec player 1's lives
            bra     .ok     ; and go to next level
.decP2
            lda     Lives2  ;then dec Player 2's lives as well
            bfl     .ok     ; if any
            dec     Lives2  ;player 1 survived so dec player 2's lives
            bra     .ok     ; and go to next level
.allDead
            lda     Lives1  ;dec P1's lives if any remain
            bfl     .chkP2
            dec     Lives1
.chkP2
            lda     PlayerTwo       ;if this is a 2player game
            bfl     .chkLives
            lda     Lives2  ;then dec Player 2's lives as well
            bfl     .chkLives       ; if any
            dec     Lives2
.chkLives
            lda     Lives1  ;if either player has lives remaining
            ora     Lives2
            bir     .3      ; start this level over for them lda     #INITSCORE
            sta     Score lda     Continues       ;everyone dead; check their continues
            beq     .badEnd         ;boo hoo, no more; game over
            jsr     ShowContinue    ;shall we continuation this travesty
            bcc     .continue       ;yes
.badEnd
            jsr     ShowCredits     ;game over
            jmp     DemoLoop
.continue
            dec     Continues jsr     InitPlayers lda     CurLevel        ;modify CurLevel to start of Level (ie Lakes)
            dec                     ; if players want to continue
            and     #$FFF0;(should be quicker)
            clc
            adc     #4
            sta     CurLevel
.3
;           stz     DeathFlag
            ldx     CurLevel        ; yes- simple! (well, remove our RTS ;)
            jmp     SetLevel
.ok
           ;jsr     ShowFINISH      ; no, show score
.no
            stz     DoneFlag
            lda     CurLevel        ;next level
```

Page # 38

ASTHMA VIDEO GAME SOURCE CODE

```
            clc
            adc     #4
            tax
            cmp     LevelMax        ; until done!
            bge     .end
            jmp     LevelLoop
    .end
            jsr     ShowVictory     ;show we reached the end!

jmp     DemoLoop        ;restart
            ;jmp    Start   ;restart

PROCEND
;IIIIIIIIIIIIIIIIIIIIIIIIIIIIIIIIIIIIIIIIIIIIIIIIIII
; Init both players lives and med stuff
;
; ENTRY:    NONE
;
; EXIT: NONE
;
; (LAI)
;IIIIIIIIIIIIIIIIIIIIIIIIIIIIIIIIIIIIIIIIIIIIIIIIIII InitPlayers     PROC lda     #INITLIVES      ;init player lives
            sta     Lives1
            sta     Lives2
            lda     #INITPFLOW      ;init peakflows each life
            sta     Peakflow1       ;init peakflows each life
            sta     Peakflow2       ;init peakflows each life
            sta     OldPeak1        ;init peakflows each life
            sta     OldPeak2        ;init peakflows each life
            stz     Cold1
            stz     Cold2
            jsr     SetBothNew
            stz     Wheeze1
            stz     Wheeze2
            lda     PlayerTwo
            btr     .cont0
            stz     Lives2
    .cont0
            lda     #INITBBS        ;init breath blasts
            sta     Weapon1         ;init weapon usage
            sta     Weapon2 lda     #INITSCORE
            sta     Score
            rts
            PROCEND

END
ASTHMA VIDEO GAME SOURCE CODE
```

I claim:

1. A method for treating a medical condition in a human patient comprising the following steps:
   a) choosing a psychological strategy for treating said medical condition;
   b) encoding electronic instructions for an interactive video game, said interactive video game being selected to said psychological strategy;
   c) loading said electronic instructions into a microprocessor-based unit equipped with a display means for displaying said interactive video game and with an input means for receiving responses to said interactive video game from said human patient; and
   d) instructing said human patient how and when to use said microprocessor-based unit to play said interactive video game.

2. The method of claim 1, wherein said psychological strategy implemented by said interactive video game comprises a graphical game character faced with fictitious challenges representative of said medical condition and said responses of said human patient to said challenges of said graphical game character define the game success of said graphical game character, thereby causing a psychological response in said human patient which will improve said medical condition.

3. The method of claim 1, wherein said psychological strategy implemented by said interactive video game comprises a graphical game character faced with fictitious game challenges, including predetermining said fictitious game challenges by a health care professional and determining the fate of said graphical game character by said responses of said human patient.

4. The method of claim 1, wherein said psychological strategy implemented by said interactive video game comprises distraction.

5. A method for treating a medical condition in a human patient comprising the following steps:
   a) choosing a set of self-care directions for treating said medical condition;
   b) encoding a first set of electronic instructions for an interactive video game, said set of self-care directions being embedded in said interactive video game;
   c) loading said first set of electronic instructions into a microprocessor-based unit equipped with a display means for displaying said interactive video game and with an input means for receiving responses to said interactive video game from said human patient; and
   d) instructing said human patient how and when to use said microprocessor-based unit to play said interactive video game.

6. The method of claim 5, wherein said set of self-care directions is being communicated to said human patient in said interactive video game by a graphical game character faced with fictitious challenges representative of said medical condition and said responses of said human patient to said challenges of said graphical game character defining the game success of said graphical game character.

7. The method of claim 5, wherein said set of self-care directions comprises a subconscious strategy for said human patient.

8. The method of claim 7, wherein said subconscious strategy is substitution and said medical condition is smoking.

9. The method of claim 7, wherein said subconscious strategy is role-playing and said medical condition is diabetes.

10. The method of claim 5, comprising the additional steps of:
    a) connecting to said micro-processor based unit a monitoring means for measuring a physical parameter of said human patient's medical condition;
    b) encoding a second set of electronic instructions for operating said monitoring means, said second set of electronic instructions being compatible with said first set of electronic instructions; and
    c) merging said second set of electronic instructions with said first set of electronic instructions.

11. The method of claim 10, wherein said interactive video game comprises a graphical game character, said graphical game character communicating said self-care directions which comprise directives about how and when to use said monitoring means while playing said interactive video game.

12. A method for treating a medical condition in a human patient comprising the following steps:
    a) choosing a set of counseling directions for treating said medical condition;
    b) encoding electronic instructions for an interactive video game, said set of counseling directions being embedded in said interactive video game;
    c) loading said electronic instructions into a microprocessor-based unit equipped with a display means for displaying said interactive video game and with an input means for receiving responses to said interactive video game from said human patient; and
    d) instructing said human patient how and when to use said microprocessor-based unit to play said interactive video game.

13. The method of claim 12, wherein said counseling directions embedded in said interactive video game comprise a graphical game character faced with fictitious challenges representative of said medical condition and said responses of said human patient to said challenges of said graphical game character define the game success of said graphical game character.

14. A method for evaluating a medical condition in a human patient comprising the following steps:
    a) encoding electronic instructions for an interactive video game, said interactive video game having a scoring procedure for quantitatively analyzing said medical condition of said human patient;
    b) delivering said electronic instructions to a microprocessor-based unit equipped with a display means for displaying said interactive video game and an input means for receiving responses to said interactive video game from said human patient; and
    c) instructing said human patient how and when to use said microprocessor-based unit to play said interactive video game.

15. The method of claim 14, wherein said scoring procedure comprises recording said responses of said human patient, assigning values to said responses, and performing a computation on said assigned values to obtain a final score, whereby said final score is used as a quantitative measure of said medical condition.

16. The method of claim 15, wherein said interactive video game comprises a graphical game character faced with fictitious challenges representative of said medical condition and said responses of said human patient to said challenges of said graphical game character define the game success of said graphical game character.

17. The method of claim 14, wherein said interactive video game comprises a graphical game character faced with fictitious challenges, said fictitious challenges being predetermined by a health care professional and said responses of said human patient determining the fate of said graphical game character.

18. The method of claim 17, wherein the fate of said graphical character is represented by said final score.

* * * * *